United States Patent
Elrayess et al.

(10) Patent No.: US 12,416,007 B2
(45) Date of Patent: Sep. 16, 2025

(54) GATA3 INHIBITORS FOR TREATING INSULIN RESISTANCE

(71) Applicant: QATAR UNIVERSITY, Doha (QA)

(72) Inventors: Mohamed Elrayess, Doha (QA); Layla Almansoori, Doha (QA)

(73) Assignee: QATAR UNIVERSITY, Doha (QA)

( * ) Notice: Subject to any disclaimer, the term of this patent is extended or adjusted under 35 U.S.C. 154(b) by 120 days.

(21) Appl. No.: 18/199,817

(22) Filed: May 19, 2023

(65) Prior Publication Data
US 2024/0026365 A1 Jan. 25, 2024

Related U.S. Application Data

(62) Division of application No. 16/909,755, filed on Jun. 23, 2020, now Pat. No. 11,976,282.

(51) Int. Cl.
| | |
|---|---|
| *C12N 15/11* | (2006.01) |
| *A61K 9/00* | (2006.01) |
| *A61P 3/10* | (2006.01) |
| *C12N 15/113* | (2010.01) |

(52) U.S. Cl.
CPC ........ *C12N 15/1138* (2013.01); *A61K 9/0014* (2013.01); *A61K 9/0019* (2013.01); *A61K 9/0053* (2013.01); *A61P 3/10* (2018.01)

(58) Field of Classification Search
CPC .............. C12N 15/1138; A61K 9/0019; A61K 9/0053; A61P 3/10
See application file for complete search history.

(56) References Cited

U.S. PATENT DOCUMENTS

| | | |
|---|---|---|
| 8,119,789 B2 | 2/2012 | Sel et al. |
| 9,249,413 B2 | 2/2016 | Schmidts et al. |
| 9,404,110 B2 | 8/2016 | Schmidts et al. |
| 9,417,243 B2 | 8/2016 | Qi et al. |
| 9,428,576 B2 | 8/2016 | Tacha et al. |
| 9,797,888 B2 | 10/2017 | Akitomi et al. |
| 10,273,526 B2 | 4/2019 | Todd et al. |
| 10,487,325 B2 | 11/2019 | Bille et al. |
| 2007/0166710 A1 | 7/2007 | Stoffel et al. |
| 2015/0216892 A1 | 8/2015 | Thibonnier |
| 2017/0298361 A1 | 10/2017 | Shaul et al. |
| 2020/0131267 A1 | 4/2020 | Carvalho et al. |

FOREIGN PATENT DOCUMENTS

| | | |
|---|---|---|
| WO | 2005/124359 A2 | 12/2005 |
| WO | 2019/217423 A1 | 11/2019 |

OTHER PUBLICATIONS

Hotamisligil, et al: "Adipose expression of tumor necrosis factor-α: Direct role in obesity-linked insulin resistance", Science; Jan. 1, 1993; vol. 259, pp. 87-91.
Hu, et al: "Berberine increases expression of GATA-2 and GATA-3 during inhibition of adipocyte differentiation", Phytomedicine 2009; vol. 16, pp. 864-873.
Hu, et al: "Berberine inhibits adipogenesis in high-fat diet-induced obesity mice", Fitoterapia 2010; vol. 81, pp. 358-366.
Huda, et al: "Genetic variation of the transcription factor GATA3, not STAT4, is associated with the risk of type 2 diabetes in the Bangladeshi population", PLOS One; Jul. 25, 2018; vol. 13(7), e0198507.
Jack, et al: "GATA proteins work together with friend of GATA (FOG) and C-terminal binding protein (CTBP) co-regulators to control adipogensis", The Journal of Biological Chemistry; Oct. 15, 2010; vol. 285(42), pp. 32405-32414.
Jaganjac, et al: "Combined metformin and insulin treatment reverses metabolically impaired omental adipogenesis and accumulation of 4-hydroxynonenal in obese diabetic patients", Redox Biology; Mar. 16, 2017; vol. 12, pp. 483-490.
Ji, et al: "Short term high fat diet challenge promotes alternative macrophage polarization in adipose tissue via natural killer T Cells and Interleukin-4", The Journal of Biological Chemistry; Jul. 13, 2012; vol. 287(29), pp. 24378-24386.
Jo, et al: "Hypertrophy and/or Hyperplasia: Dynamics of Adipose Tissue Growth", PLOS Computational Biology; Mar. 27, 2009; vol. 5(3), e1000324; doi:10/371/journal.pcbi.1000324.
Joulin, et al: "A T Cell specific TCR & DNA binding protein is a member of the human GATA family", The EMBO Journal 1991; vol. 10(7), pp. 1809-1816.
Kahn, et al: "Mechanisms linking obesity to insulin resistance and type 2 diabetes", Nature Insight Review; Dec. 14, 2006; vol. 444, pp. 840-846; doi:10.1038/nature05482.
Karri, et al: "Natural anti-obesity agents and their therapeutic role in management of obesity: A future trend perspective", Biomedicine & Pharmacotherapy 2019; vol. 110, pp. 224-238.
Khan, et al: "Metabolic dysregulation and adipose tissue fibrosis: Roel of collagen VI", Molecular and Cellular Biology; Mar. 2009; vol. 29(6), pp. 1575-1591.
Kim, et al: "Identification of Creb314 as an essential negative regulator of adipogenesis", Cell Death and Disease 2014; vol. 5(e), pp. 1-13.
King, et al: "Global burden of diabetes 1995-2025 Prevalence, numberical estimates, and projections", Diabetes Care, Sep. 9, 1998; vol. 21(9), pp. 1414-1431.
King, et al: "The role of inflammatory cytokines in diabetes and its complications", The Journal of Periodontology; Aug. 1, 2008; vol. 79(8S), pp. 1527-1534.
Ko, et al: "DNA-Binding specificities of the GATA transcription factor family", Molecular and Cellular Biology, Jul. 1993; vol. 13(7), pp. 4011-4022.
Kopelman: "Obesity as a medical problem", Insight Review Article, Nature; Apr. 6, 2000; vol. 404, pp. 635-643.
Krause, et al: "Quantitative assessment of adipocyte differentiation in cell culture", Adipocyte 2016; vol. 5(4), pp. 352-358.

(Continued)

*Primary Examiner* — Gyan Chandra

(74) *Attorney, Agent, or Firm* — Squire Patton Boggs (US) LLP

(57) ABSTRACT

Methods and compositions using dnayzme-based GATA3 inhibitors for the treatment of insulin resistance and Type II diabetes, for the stimulation of adipogenesis in vivo, and for the promotion of fat redistribution are disclosed.

10 Claims, 4 Drawing Sheets

Specification includes a Sequence Listing.

(56) References Cited

OTHER PUBLICATIONS

Lee, et al: "Adipose tissue heterogeneity: Implication of depot differences in adipose tissue for obesity complications", Molecular Aspects of Medicine; Oct. 13, 2012; vol. 34, pp. 1-11.
Li, et al: "Bio-informatics analysis of a gene co-expression module in adipose tissue containing the diet-responsive gene Nnat", BMC Systems Biology 2010; vol. 4(175), pp. 1-11.
Da Silva Lima, et al: "Modulatory effects of Guarana (*Paullinia cupana*) on adipogenesis", Nutrients 2017; vol. 9 (635), pp. 1-11.
Longo, et al: "Adipose tissue dysfunction as determinant of obesity-associated metabolic complications", International Journal of Molecular Sciences; May 13, 2019; vol. 20, 2358; doi: 10.3390/ijms20092358.
Lumeng, et al: "Obesity induces a phenotypic switch in adipose tissue macrophage polarization", The Journal of Clinical Investigation; Jan. 2, 2007; vol. 117(1), pp. 175-184.
Lynch, et al: "Adipose tissue invariant NKT cells protect against diet-induced obesity and metabolic disorder through regulatory cytokine production", Immunity; Sep. 21, 2012; vol. 37(3), pp. 574-587.
Mahanta, et al: "Lower expression of GATA3 and T-bet correlates with downregulated IL-10 in severe falciparum malaria", Clinical & Translational Immunology; Nov. 6, 2015; vol. 4, e49.
Makki, et al: "Adipose tissue in obesity-related inflammation and insulin resistance: cells, cytokines, and chemokines", ISRN Inflammation; Dec. 22, 2013; vol. 2013; Article ID139239, 12 pages.
McArdle, et al: "Mechanisms of obesity-induced inflammation and insulin resistance; insights into the emerging role of nutritional strategies", Frontiers in Endocrinology; May 10, 2013; vol. 4(52), pp. 1-23.
Meissburger, et al: "Adipogenesis and insulin sensitivity in obesity are regulated by retinoid-related orphan receptor gamma", EMBO Molecular Medicine 2011; vol. 3, pp. 637-651.
Moseti, et al: "Molecular regulation of adipogenesis and potential anti-adipogenic bioactive molecules", International Journal of Molecular Sciences; Jan. 19, 2016; vol. 17(124), pp. 1-24.
Mota De Sa, et al: "Transcriptional regulation of adipogensis", Comprehensive Physiology; Apr. 2017; vol. 7, pp. 635-674.
Neels, et al: "Inflamed fat: what starts the fire?", Journal of Clinical Investigation; Jan. 2006; vol. 116(1), pp. 33-35.
Nomura, et al: "Pyrrothiogatain acts as an inhibitor of GATA family proteins and inhibits the Th2 cell differentiation in vitro", Scientific Reports 2019; vol. 9(17335).
Odegaard, et al: "Mechanisms of macrophage activation in obesity-induced insulin resistance", Nat Clin Pract Endocrinol.; Nov. 2008; vol. 4(11), pp. 619-626.
Odegaard, et al: "Type 2 responses at the interface between immunity and fat metabolism", Curr Opin Immunol.; Oct. 2015; vol. 36, pp. 67-72.
Okuno, et al: "Troglitazone increases the number of small adipocytes without the change of white adipose tissue mass in obese zucker rats", Journal of Clinical Investigation; Mar. 1998; vol. 101(6), pp. 1354-1361.
Ouyang, et al: "Inhibition of Th1 development mediated by GATA-3 through an IL-4-independent mechanism", Immunity; Nov. 1998; vol. 9, pp. 745-755.
Pedroso, et al: "Inactivation of SOCS3 in leptin receptor-expressing cells protects mice from diet-induced insulin resistance but does not prevent obesity", Molecular Metabolism; Jun. 12, 2014; vol. 3, pp. 608-618.
Qiang, et al: "The obesity-induced transcriptional regulator TRIP-Br2 mediates visceral fat endoplasmic reticulum stress-induced inflammation", Nature Communications; Apr. 26, 2016; DOI: 10.1038/ncomms11378.
Radcke, et al: "A systematic review of the prevalence of mildly abnormal liver function tests and associated health outcomes", European Journal of Gastroenterology and Hepatology 2015; vol. 27(1), pp. 1-7.

Rangwala, et al: "Genetic modulation of PPARy Phosphorylation regulates insulin sensitivity", Developmental Cell; Oct. 2003; vol. 5, pp. 657-663.
Ray, et al: "Th2 cells and GATA-3 in asthma: new insights into the regulation of airway inflammation", The Journal of Clinical Investigation; Oct. 1999; vol. 104(8), pp. 985-993.
Rochford, et al: "ETO/MTG8 is an inhibitor of C/EBPB activity and a regulator of early adipogenesis", Molecular and Cellular Biology; Nov. 2004; vol. 24(22), pp. 9863-9872.
Ryden, et al: "Transplanted bone marrow-derived cells contribute to human adipogenesis", Cell Metabolism, Clinical and Translational Report; Sep. 1, 2015; vol. 22, pp. 408-417.
Seki, et al: "IL-4-induced GATA-3 expression is a time-stricted instruction switch for Th2 cell differentiation", The Journal of Immunology 2004; vol. 172, pp. 6158-6166.
Sel, et al: "Effective prevention and therapy of experimental allergic asthma using a GATA-3-specific DNAzyme", Journal Allergy Clin Immunol; Mar. 6, 2008; vol. 121(4); pp. 910-916e.
Sell, et al: "Adipose tissue inflammation: novel insight into the role of macrophages and lymphocytes", Current Opinion in Clinical Nutrition and Metabolic Care 2010; vol. 13, pp. 366-370.
Shi, et al: "A glucocorticoid-induced leucine-zipper protein, GILZ, inhibits adipogenesis of mesenchymal cells", EMBO Reports; Mar. 14, 2003; vol. 4(4), pp. 374-380.
Shin, et al: "Macrophage VLDLR mediates obesity-induced insulin resistance with adipose tissue inflammation", Nature Communications 2017; vol. 8(1087); doi:10.1038/s41467-017-01232-w.
Shoemaker, et al: "GATA-3 directly remodels the IL-10 Locus independently of IL-4 in CD4+ T Cells", The Journal of Immunology 2006; vol. 176, pp. 3470-3479.
Shulman, "Cellular mechanisms of insulin resistance", Journal of Clinical Investigation 2000; vol. 106(2), pp. 171-176.
Smith, et al: "Adipose tissue regulates insulin sensitivity: Role of adipogenesis, de novo lipogenesis and novel lipids", Journal of Internal Medicine; Nov. 2016; vol. 280(5), pp. 465-475; doi:10.1111/joim. 12540.
Snel, et al: "Ectopic fat and insulin resistance: Pathophysiology and effect of diet and lifestyle interventions", International Journal of Endocrinology 2012; vol. 2012, Article ID 983814, 18 pages; doi: 10.1155/2012/983814.
Stefanon, et al: "Hydroxytyrosol, an ingredient of olive oil, reduces triglyceride accumulation and promotes lipolysis in human primary visceral adipocytes during differentiation", Experimental Biology and Medicine 2016; vol. 241, pp. 1796-1802.
Tencerova, et al: "Experimental hyperglycemia induces an increase of Monocyte and T-Lymphocyte content in adipose tissue of healthy obese women", PLOS One, Apr. 20, 2015; vol. 10(3), e0122872.
"The World Health Report 2002: Reducing Risks, Promoting Healthy Life", World Health Organization; 230 pages.
Tilg, et al: "Adipocytokines; mediators linking adipose tissue, inflammation and immunity", Nature Reviews; Sep. 22, 2006; vol. 6, pp. 772-783.
Tong, et al: "Function of GATA transcription factors in preadipocyte-adipocyte transition", Science; Oct. 6, 2000; vol. 290, pp. 134-138.
Tong, et al: "GATA transcription factors and fat cell formation", Drug News & Perspectives 2003; vol. 16(9), p. 585.
Tong, et al: "Interaction between GATA and the C/EBP family of transcription factors is critical in GATA-mediated suppression of adipocyte differentiation", Molecular and Cellular Biology; Jan. 2005; vol. 25(20, pp. 706-715.
Tontonoz, et al: "Stimulation of adipogenesis in fibroblasts by PPARy2, a Lipid-activated transcription factor", Cell; Dec. 30, 1994; vol. 79, pp. 1147-1156.
Van Der Wijden, et al: "The relationship between moderate-to-vigorous intensity physical activity and insulin resistance, insulin-like growth factor (IGF-1)-system 1, leptin and weigth change in healthy women during pregnancy and after delivery", Clinical Endocrinology 2015; vol. 82, pp. 68-75.
Van Esch, et al: "GATA3 haplo-insufficiency causes human HDR syndrome", Letters to Nature, Jul. 27, 2000; vol. 406, pp. 419-422.
Van Hamburg, et al: "Enforced expression of GATA3 allows differentiation of IL-17-producing cells, but constrains Th17-mediated pathology", European Journal of Immunology 2008; vol. 38, pp. 2573-2586.

(56) References Cited

OTHER PUBLICATIONS

Vigouroux, et al: "Molecular mechanisms of human lipodystrophies: From adipocyte lipid droplet to oxidative stress and lipotoxicity", The International Journal of Biochemistry and Cell Biology; Mar. 8, 2011; vol. 43, pp. 862-876.
Villarroya, et al: "Toward an understanding of how immune cells control brown and beige adipobiology", Cell Metabolism; May 1, 2018; vol. 27, pp. 954-961.
Virtue, et al: "Adipose tissue expandability, lipotoxicity and the Metabolic Syndrome—An allostatic perspective", Biochimica Acta; Jan. 6, 2010; vol. 1801, pp. 338-349.
Vishvanath, et al: "Contribution of antipogenesis to healthy adipose tissue expansion on obesity", The Journal of Clinical Investigation; Review Series: Mechanisms Underlying The Metabolic Syndrome; Oct. 2019; vol. 129(10), pp. 4022-4031.
Wan, et al: "GATA3: a master of many trades in immune regulation", Trends in Immunology, Cell Press; Jun. 2014; vol. 35(6), pp. 233-242.
Wang, et al: "An essential role of the transcription factor GATA-3 for the function of regulatory T cells", Immunity; Sep. 23, 2011; vol. 35(3), pp. 337-348.
Wang, et al: "Wnt/B-catenin mediates AICAR effect to increase GATA3 expression and inhibit adipogenesis", The Journal of Biological Chemistry; Aug. 7, 2015; vol. 290(32), pp. 19458-19468.
Weisberg, et al: "Obesity is associated with macrophage accumulation in adipose tissue", Journal of Clinical Investigations 2003; vol. 112, pp. 1796-1808.
Wellen, et al: "Inflammation, stress, and diabetes", The Journal of Clinical Investigation; May 2015; vol. 115(5), pp. 1111-1119.
Wu, et al: "Cross-regulation of C/EBPa and PPARy controls the transcriptional pathway of adipogenesis and insulin sensitivity", Molecular Cell; Feb. 1999; vol. 3, pp. 151-158.
Xie, et al: "Interactive changes between macrophages and adipocytes", Clinical and Vaccine Immunology; Apr. 2010; vol. 17(4), pp. 651-659.
Xu, et al: "Chronic inflammation in fat plays a crucial role in the development of obesity-related insulin resistance", Journal of Clinical Investigation 2003; vol. 112, pp. 1821-1830.
Xu, et al: "GATA3, HDAC6, and BCL6 regulate FOX3P+ TREG Plasticity and determine TREG conversion into elthern novel and elantigen-presenting cell-like TREG or TH1-TREG", Frontiers in Immunology; Jan. 26, 2018; vol. 9, Article 45, pp. 1-23.
Xue, et al: "Adipose deficiency of Nrf2 in ob/ob mice results in severe metabolic syndrome", Diabetes Original Article; Mar. 2013; vol. 62, pp. 845-854.
Yagi, et al: "An updated view on transcription factor GATA3-mediated regulation of Th1 and Th2 cell differentiation", International Immunology; Jun. 1, 2011; vol. 23(7), pp. 415-420.
Yamashita, et al: "Essential role of GATA3 for the maintenance of Type 2 helper T (Th2) cytokine production and chromatin remodeling at the Th2 cytokine Gene *Loci*", The Journal of Biological Chemistry; Jun. 25, 2004; vol. 279 (26), pp. 26983-26990.
Yang, et al: "Evidence of impaired adipogenesis in insulin resistance", Biochemical and Biophysical Research Communications 2004; vol. 317, pp. 1045-1051.
Yang, et al: "Pathological conditions re-shape physiological Tregs into pathological Tregs", Burns & Trauma 2105; vol. 3(1), pp. 1-11.
Zeitvogel, et al: "GATA3 regulates FLG and FLG2 expression in human primary keratinocytes", Scientific Reports; Sep. 19, 2017; vol. 7, 11847, 11 pages.
Al-Sulaiti, et al: "Mediators of impaired adipogenesis in obesity-associated insulin resistance and T2DM", IntechOpen, Adipose Tissue—An Update; pp. 1-26; doi:http://dx.doi.org/10.5772/intechopen.88746.
Al-Sulaiti, et al: "Metabolic signature of obesity-associated insulin resistance and type 2 diabetes", Journal of Translational Medicine 2019; vol. 17(348), pp. 1-11.

Al-Sulaiti, et al: "Triglyceride proflling in adipose tissues from obese insulin sensitive, insulin resistant and type 2 diabetes mellitus individuals", Journal of Translational Medicine 2018; vol. 16(175), pp. 1-13.
Almuraikhy, et al: "Interleukin-6 induces impairment in human subcutaneous adipogenesis in obesity-associated insulin resistance", Diabetologia; Jun. 24, 2016: vol. 59, pp. 2406-2416.
Asch-Kendrick, et al: The role of GATA3 in breast carcinomas: A Review:, Human Pathology 2015, doi: 10.1016/j.humanpath.2015.09.035.
Batchvarova, et al: "Inhibition of adipogenesis by the stress-induced protein CHOP (Gadd153)", The EMBO Journal 1995; vol. 14(19), pp. 4654-4661.
Bezy, et al: "Delta-interacting protein A, a new inhibitory partner of CCAAT/enhancer-binding Protein B Implicated in Adipocyte differentiation", The Journal of Biological Chemistry; Mar. 25, 2005; vol. 280(12), pp. 11432-11438.
Blokzijl, et al: "Physical and functional interaction between GATA-3 and Smad3 allows TGF-Regulation of GATA Target Genes", Current Biology; Jan. 8, 2002; vol. 12, p. 35-45.
Burzyn, et al: "Regulatory T Cells in non-lymphoid tissues", Nat Immunol.; Oct. 2013; vol. 14(10), pp. 1007-1013.
Cancello, et al: "Increased infiltration of macrophages in omental adipose tissue is associated with marked hepatic lesions in morbid human obesity", Diabetes; Jun. 2006; vol. 55, pp. 1554-1561.
Cao, et al: "Regulated expression of three C/EBP isoforms during adipose conversion of 3T3-L1 cells", Genes & Development 1991; vol. 5, pp. 1538-1552.
Cao, et al: "Yeast B-glucan suppresses the chronic inflammation and improves the microenvironment in adipose tissues of ob/ob mice", Journal of Agricultural and Food Chemistry; Dec. 29, 2017; doi: 10.1021/acs.jafc.7b04921.
Cawthorn, et al: "Adipose tissue stem cells meet preadipocyte commitment: going back to the future", Journal of Lipid Research 2012; Dec. 1, 2011; vol. 53, pp. 227-246.
Cawthorn, et al: "Tumour necrosis factor-a inhibits adipogenesis via a B-catenin/TCF4(TCF7L2)-dependent pathway", Cell Death Differ., Jul. 2007; vol. 14(7), pp. 1361-1373.
Chen, et al: "GATA3 as master regulator and therapeutic target in ovarian high-grade serous carcinoma stem cells", International Journal of Cancer, Jul. 14, 2018; https://doi.org/10.1002/ijc.31750.
Chen, et al: "Mature miR-183, negatively regulated by transcription factor GATA3, promotes 3T3-L1 adipogenesis through inhibition of the canonical Wnt/B-catenin signaling pathway by targeting LRP6", Cellular Signalling; Feb. 18, 2014; vol. 26, pp. 1155-1165.
Chen, et al: "Mechanisms linking inflammation to insulin resistance", International Journal of Endocrinology 2015; vol. 2015, Article ID 508409, 9 pages.
Chen, et al: "Treatment of allergic inflammation and hyperresponsiveness by a simple compound, Bavachinin, isolated from Chinese herbs", Cellular & Molecular Immunology; Sep. 9, 2013; vol. 10, pp. 497-505.
Cho, et al: "Adipose tissue dendritic cells are independent contributors to obesity-induced inflammation and insulin resistance", J. Immunol; Nov. 1, 2016; vol. 197(9), pp. 3650-3661.
Choe, et al: "Adipose tissue remodeling: Its role in energy metabolism and metabolic disorders", Frontiers in Endocrinology; Apr. 13, 2016; vol. 7, Article 30.
Choe, et al: "Macrophage HIF-2a ameliorates adipose tissue inflammation and insulin resistance in obesity", Diabetes; Oct. 2014; vol. 63, pp. 3359-3371.
Cipolletta, et al: "PPARy is a major driver of the accumulation of phenotype of adipose tissue T reg Cells", Nature, Jun. 28, 2012; vol. 486(7404), pp. 549-553.
Colitti, et al: "Different anti-adipogenic effects of bio-compounds on primary visceral pre-adipocytes and adipocytes", EXCLI Journal; Jun. 20, 2016; vol. 15, pp. 362-377.
Derosa, et al: "Adipose tissue dysfunction and metabolic disorders: Is it possible to predict who will develop type 2 diabetesmellitus? Role of markErs in the progresSion of Dlabetes in obese paTieNts (The RESISTIN trial", Cytokine 2020; vol. 127, 154947.

(56) References Cited

OTHER PUBLICATIONS

Dubois, et al: "Decreased expression of adipogenic genes in obese subjects with Type 2 diabetes", Obesity (Silver Spring); Sep. 2006; vol. 14(9), pp. 1543-1552.

El Arabey, et al: "GATA3 as a master regulator for interactions of tumor-associated macrophages with high-grade serous ovarian carcinoma", Cellular Signalling; Jan. 11, 2020; vol. 68, Article 109539.

Elrayess, et al: "4-hydroxynonenal causes impairment of human subcutaneous adipogenesis and induction of adipocyte insulin resistance", Free Radical Biology & Medicine 2017; Author's Accepted Manuscript, http://dx.doi.org/10.1016/j.freeradbiomed.2017.01.015.

Farmer, "Transcriptional control of adipocyte formation", Cell Metabolism; Oct. 2006; vol. 4, pp. 263-273.

Ferber, et al: "GATA-3 significantly downregulates IFN-y production from developing Th1 cells in addition to inducing IL-4 and IL-5 levels", Clinical Immunology; May 1999; vol. 91(2), pp. 134-144.

Feuerer, et al: "Lean, but not obese, fat is enriched for a unique population of regulatory T cells that affect metabolic parameters", Nature Medicine; Jul. 26, 2009; vol. 15(8), pp. 930-940.

Fokina, et al: "DNA enzymes as potential therapeutics: Towards clinical application of 10-23 DNAzymes", Expert Opinion on Biological Therapy; Mar. 14, 2015; vol. 15, No. 5, pp. 689-711.

Frieler, et al: "Nuclear receptor control of opposing macrophagephenotypes in cardiovascular disease", Frontiers in Bioscience; Jan. 1, 2012; vol. 17, pp. 1917-1930.

Garn, et al: "GATA-3-specific DNAzyme—a novel approach for stratified asthma therapy", European Journal of Immunology 216; doi: 10.1002/eji.201646450.

Ghonim, et al: "PARP is activated in human asthma and its inhibition of olaparib blocks house dust mite-induced disease in mice", Clinical Science 2015; vol. 129, pp. 951-962.

Gregoire, et al: "Understanding adipocyte differentiation", Physiological Reviews; Jul. 1998; vol. 78(3), pp. 783-809.

Goossens, et al: "Expression of NLRP3 inflammasome and T cell population markers in adipose tissue are associated with insulin resistance and impaired glucose metabolism in humans", Molecular Immunology 2012; vol. 50, pp. 142-149.

Grundy, et al: "Definition of Metabolic Syndrome: Report of the National Heart, Lung, and Blood Institute/American Heart Association Conference on Scientific Issues Related to Definition; NHLBI/AHA Proceedings", Arteriosclerosis, Thrombosis, and Vascular Biology; Feb. 1, 2004; vol. 24(2), pp. e13-e18.

Guan, et al: "GATA binding protein 3 is correlated with leptin regulation of PPARy1 in hepatic stellate cells", J. Cell. Mol. Med. 2017; vol. 21(3), pp. 568-578.

Guilherme, et al: "Adipocyte dysfunctions linking obesity to insulin resistance and type 2 diabetes", Nat. Rev. Mol. Cell Biol.; May 2008; vol. 9(5), pp. 367-377.

Gupta, et al: "Transciptional control of preadipocyte determination by Zfp423", Nature Letters; Mar. 2010, vol. 464, pp. 619-625.

Gustafson, et al: "Insulin resistance and impaired adipogenesis", Cell Press Review; Apr. 2015; vol. 26(4), pp. 193-200.

Ham, et al: "Macrophage Glucose-6-Phosphate Dehydrogenase stimulates proinflammatory responses to oxidative stress", Molecular and Cellular Biology; Jun. 2013; vol. 33(12), pp. 2425-2435.

Hammarstedt, et al: "WISP2 regulates preadipocyte commitment and PPARy activation by BMP4", PNAS; Feb. 12, 2013; vol. 110(7), pp. 2563-2568.

Han, et al: "IL-33 Reverses an obesity-induced deficit in visceral adipose tissue ST2+ T Regulatory cells and Ameliorates adipose tissue inflammation and insulin resistence", The Journal of Immunology; Apr. 13, 2015; vol. 194, pp. 4777-4783.

Hauner: "The new concept of adipose tissue function", Physiology & Behavior 2004; vol. 83, pp. 653-658.

Helaleh, et al: "Association of polybrominated diphenyl ethers in two fat compartments with increased risk of insulin resistance in obese individuals", Chemosphere; Jun. 18, 2018; vol. 209, pp. 268-276.

Ho, et al: "GATA3 and the T-cell lineage: essential functions before and after T-helper-2-cell differentiation", Nat Rev Immunol; Feb. 2009; vol. 9(2), pp. 125-135.

Hocking, et al: "Adiposity and insulin resistance in humans: The role of the different tissue and cellular lipid depots", Endocrine Reviews; Apr. 2, 2013; vol. 34(4), pp. 463-500.

Homburg, et al: "Safety and tolerability of a novel inhaled GATA3 mRNA targeting DNAzyme in patients with Th2-driven asthma", Letter to the Editor, J. Allergy Clin Immunol 2015; http://dx.doi.org/10.1016/j.jaci.2015.02.018.

Hong, et al: "The ethanol extract of Holotrichia diomphalia larvae, containing fatty acides and amino acids, exerts anti-asthmatic effects through inhibition of the GATA-3/Th2 Signaling pathway in asthmatic mice", Molecules, Feb. 28, 2019; vol. 24(852); doi: 10.3390/molecules24050852.

GATA3 INHIBITORS FOR TREATING INSULIN RESISTANCE

CROSS-REFERENCE TO RELATED APPLICATION(S)

This application is a divisional application of U.S. patent application Ser. No. 16/909,755 filed on Jun. 23, 2020, the entire content of which is incorporated by reference.

REFERENCE TO ELECTRONIC SEQUENCE LISTING

The application contains a Sequence Listing which has been submitted electronically in .XML format and is hereby incorporated by reference in its entirety. Said XML copy, created on Sep. 5, 2023, is named "432743.10347ST26.xml" and is 203,704 bytes in size. The sequence listing contained in this XML file is part of the specification and is hereby incorporated by reference herein in its entirety.

FIELD OF INVENTION

Provided herein are methods relating to the use of GATA3 inhibitors for the treatment of insulin resistance and related disorders and diseases, including Type II diabetes, as well as to methods for using GATA3 inhibitors to stimulate adipogenesis in vivo and to stimulate fat redistribution from visceral deposits to subcutaneous deposits in desirable locations in the body.

BACKGROUND

GATA3

GATA3 is part of the GATA family of transcription factors, which play roles in controlling expression in a wide variety of genes. The GATA3 gene is comprised of six exons encoding a transcription factor with two transactivation domains and two zinc finger domains (see, e.g., Joulin et al., *EMBO J.*, 10(7):1809-16 (1991), Yamashita et al., *JBC*, 279(26):26983-(2004), and Van Esch et al., *Nature*, 406 (6794):419-22 (2000), that binds to the consensus sequence 5'-WGATAG-3', and is expressed in T cells, mast cells, basophils, epithelial cells and fat cells, including white adipocyte precursors. The role of GATA3 in Treg cellular plasticity and conversion into Th1-Treg or APC-T-reg has been extensively characterized (Xu et al., *Front. Immunol.*, 9:45 (2018)).

GATA3 is necessary for the development of MHC II-restricted CD4 T cells from CD4+ cells. It is also associated with normal development of various tissues including the skin, fat cells, the thymus, and the nervous system. GATA3 is expressed in a range of cells found in adipose tissues, including preadipocytes, mature adipocytes and various inflammatory cells.

GATA3's role in the conversion of CD4+ cells into TH2 cells has been utilized in the design of asthma therapies, based on the inhibition of GATA3 to prevent inflammatory diseases. A variety of GATA3 inhibitors have been used as therapeutic compositions.

Hong et al., reported that ethanol extracts of *Holotrichia diomphalia* reduced GATA3 expression in lungs in a mouse model of allergic asthma. Ghonim et al. reported that administration of the drug olaparib reduced GATA3 expression in a mouse asthma model (Ghonim et al., *Clin. Sci.*, 29(11): 951-62 (2015)). The naturally occurring small molecule bavachinin has also been found to reduce GATA3 expression in the mouse asthma model (Chen et al., *Cellular and Molecular Immunology*, 10:497-505 (2013)). Sel et al (2008) *J. Allergy Clin. Immunol.*, 121(4):910-916, describes the use of the dnazyme-based GATA3 inhibitor gd21 to prevent airway inflammation and mucus production and inhibit development of airway hyperresponsiveness to methacholine in models of acute allergic airway inflammation.

Dnazyme-based GATA3 inhibitors are also used to target other TH2-based inflammatory-related diseases. SB011, from Sterna Biologicals, is a DNAzyme that targets GATA3 and cleaves its messenger RNA. It is currently in Phase II clinical trials as both part of an inhalant therapy for the treatment of asthma and chronic obstructive pulmonary disease (COPD). It is also currently in Phase II studies as part of a composition for topical administration for the treatment of atopic dermatitis. Patents U.S. Pat. Nos. 9,249, 413 and 9,404,110 are directed to pharmaceutical compositions for topical application comprising DNAzymes with GATA3 inhibitory activity with defined sequences. A second dnazyme-based pharmaceutical with GATA3 inhibitory activity by Sterna, SB012, is in Phase II trials as a treatment for active ulcerative colitis.

In addition to being involved in TH2-based inflammatory responses, GATA3 has been identified as a factor associated with obesity (Tong et al., *Science*, 290(5489):134-8 (2000)). GATA3 forms protein complexes with CCAAT/enhancer binding proteins alpha (C/EBPa) and beta (C/EB113), members of a family of transcription factors that are integral to adipogenesis. GATA3 expression is be upregulated in insulin resistant obese individuals in comparison to insulin sensitive of similar weight (Almuraikhy et al., *Diabetologia*, 59:2406-16 (2016)). There is a clear need for improved strategies to treat for the treatment of obesity-related diseases and conditions, and, GATA3 is an attractive therapeutic target for the development of new therapies to reverse insulin resistance and lower the risk of Type II diabetes.

SUMMARY OF THE INVENTION

Provided herein are methods for treatment of insulin resistance and related diseases and disorders thereof by inhibiting GATA3 expression. In some embodiments, GATA3 expression inhibited by administration of an effective amount of a GATA3 inhibitor. GATA3 inhibitors of the disclosure include small molecules, antibodies, dnayzmes or siRNAs. One or more GATA3 inhibitors can be used in therapeutic compounds of the disclosure. In certain embodiments, the GATA3 inhibitor is a dnazyme, e.g., hgd40. In some embodiments is a human patient.

Also provided herein are methods of stimulating adipogenesis in an individual by inhibiting GATA3 expression. In some embodiments GATA3 expression is inhibited by administration of an effective amount of a GATA3 inhibitor. GATA3 inhibitors for stimulating adipogenesis include small molecules, antibodies, dnayzmes siRNAs. Of particular interest is the use of GATA3-inhibiting dnayzmes to stimulate adipogenesis in individuals. In some embodiments, the dnazyme is hgd40.

Also provided herein are methods of stimulating fat redistribution from one or more visceral adipose tissue deposits in a human patient to a desired subcutaneous target site in said patient by administration of an effective amount of one or more GATA3 inhibitors to a site at or adjacent to the desired target site for fat redistribution. In some embodiments, the fat redistribution is mediated by the administration of one or more GATA3 inhibitors in, at or adjacent to a tissue where increased adipogenesis is desired. GATA3 inhibitors for stimulating fat redistribution include small molecules, antibodies, dnayzmes siRNAs. Of particular interest is the use of GATA3-inhibiting dnazymes to stimulate adipogenesis in individuals. In some embodiments the dnazyme is hgd40.

DETAILED DESCRIPTION

Definitions

Figure 1:
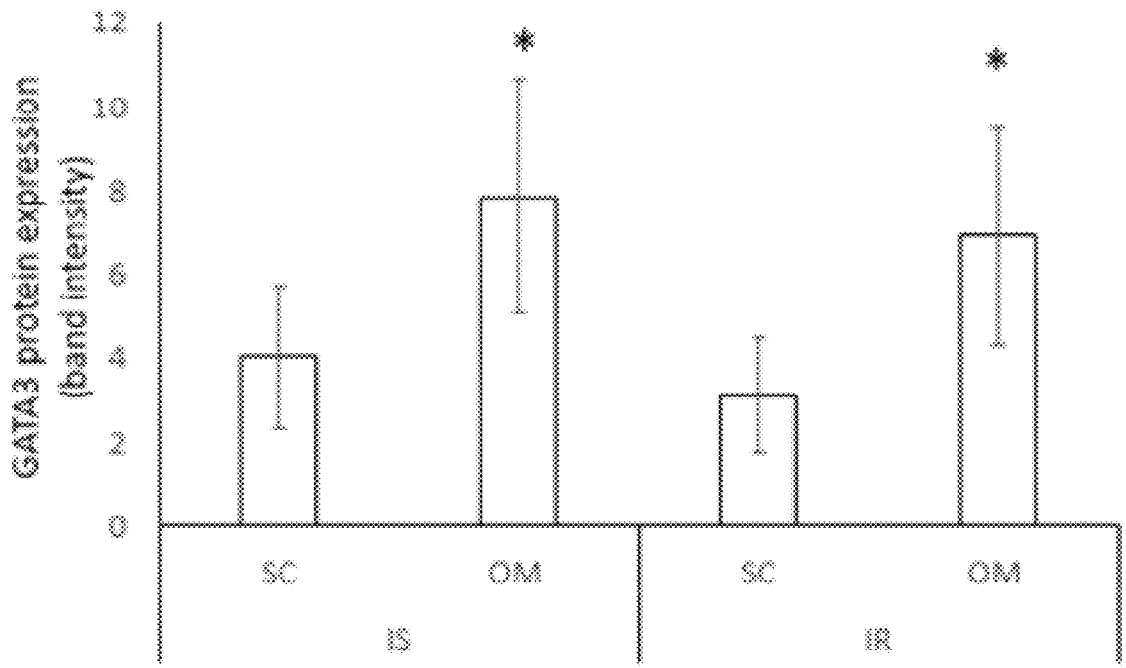
FIG. 1 shows GATA3 expression in subcutaneous (SC) and omental (OM) tissues by Western blotting.

When referring to the compounds and methods provided herein, the following terms have the meanings as defined herein. Unless defined otherwise, all technical and scientific terms used herein have the same meaning as is commonly understood by one of ordinary skill in the art. In the event that multiple definitions for a term are used herein, definitions in this section will prevail, unless otherwise stated. The techniques and procedures described or referenced herein are generally understood and commonly employed using conventional methodologies described in Green and Sambrook, Molecular Cloning: A Laboratory Manual 4$^{th}$ ed. (2012), Cold Spring Harbor Laboratory Press, Cold Spring harbor, NY; Ausubel et al., Current Protocols in Molecular Biology, John Wiley & Sons; and Rosenberg et al. As appropriate, procedures involving the use of commercially available kits and reagents are generally carried out in accordance with manufacturer-defined protocols and conditions unless otherwise noted.

As used herein, the singular forms "a," "an," and "the" include the plural references unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value. For logarithmic scale, "about" indicates a designated value ±0.1 or ±0.2 log units.

"Treating" or "treatment" of any disease or disorder refers, in certain embodiments, to ameliorating a disease or disorder, either physically (e.g., stabilization of a discernable symptom) or physiologically (e.g., stabilization of a physical parameter) or both. In yet another embodiment, "treating" or "treatment" of a disease refer to executing a protocol, which may include administering one or more therapeutic agents to an individual (human or otherwise), in an effort to obtain beneficial or desired results in an individual, including clinical and cosmetic results. Beneficial or desired clinical results include, but are not limited to, alleviation or amelioration of one or more symptoms, diminishment of extent of disease(s), stabilized (i.e., not worsening) state of disease, preventing spread or increase in severity of disease, delay or slowing of disease progression, amelioration or palliation of the disease state, and remission (whether partial or total). "Treatment" can also mean prolonging survival as compared to expected survival of an individual not receiving treatment. Further, "treating" and "treatment" may occur by administration of one dose of a therapeutic agent or therapeutic agents, may occur by administration of one dose of a therapeutic agent or therapeutic agents, or may occur upon administration of a series of doses of a therapeutic agent or therapeutic agents. "Treating" or "treatment" does not require complete alleviation of signs or symptoms, and does not require a cure. "Treatment" can also refer to clinical intervention, such as administering one or more therapeutic agents to an individual, designed to alter the natural course of the individual being treated (i.e., to alter the course of the individual that would occur in absence of the clinical intervention).

As used herein, "cosmetic" refers to a beautifying substance or preparation, which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more conditions, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

The term "apply" or "application" as used in reference to a composition, means to apply or spread the compositions of the present invention onto a substrate such as the human skin surface or epidermis.

As used herein, "topical application" means directly laying on or spreading on outer skin or the scalp, e.g., by use of the hands or an applicator such as a wipe, roller, or spray.

The term "dermatologically acceptable" as used herein means that the compositions or components described are suitable for use in contact with human skin tissue without undue toxicity, incompatibility, instability, allergic response, and the like.

The term "safe and effective amount" as used herein means an amount of a compound or composition sufficient to significantly induce a positive benefit.

As used herein, the terms "prophylactic agent" and "prophylactic agents" refer to any agent(s) which can be used in the prevention of a condition, disease, or disorder or one or more symptoms thereof. In certain embodiments, the term "prophylactic agent" includes a compound provided herein. In certain other embodiments, the term "prophylactic agent" does not refer to a compound provided herein. In certain embodiments, a prophylactic agent can be an agent which is known to be useful for, or has been or is currently being used to prevent or impede the onset, development, progression and/or severity of a condition, disease, or disorder associated with insulin resistance, or which is known to be useful for, or has been or is currently used to prevent or impede the onset of side effects or reduce the severity of side effects.

An "effective amount" of an agent disclosed herein is an amount sufficient to carry out a specifically stated purpose. An "effective amount" may be determined empirically and in a routine manner, in relation to the stated purpose. An "effective amount" or an amount "sufficient" of an agent is that amount adequate to produce a desired biological effect, such as a beneficial result, including a beneficial clinical result. In some embodiments, the term "effective amount" refers to an amount effective to "treat" a disease or disorder in an individual (e.g., a mammal such as a human).

As used herein, the term "therapeutically effective amount" or "effective amount" refers to amount of a protein, nucleic acid, oligonucleotide, or composition that, when administered to a subject is effective to treat a disease or disorder. In some embodiments, a therapeutically effective amount of a composition that, when administered to a subject is effective to prevent or ameliorate a disease or progression of the disease, or result in amelioration of symptoms. The term "therapeutic agent" can refer to one or more GATA3 inhibitors, or combinations or compositions thereof.

As used herein, the phrase "prophylactically effective amount" refers to the amount of a therapy (e.g., prophylactic agent) which is sufficient to result in the prevention or reduction of the development, recurrence or onset of one or more symptoms associated with a condition, disease, or disorder, or reduce or prevent side effects, or to enhance or improve the prophylactic effect(s) of another therapy (e.g., another prophylactic agent).

"Administration" and variants thereof (in some embodiments, "administering" a compound) in reference to a compound, e.g., a GATA3 inhibitor, means introducing the compound or a prodrug of the compound, or a population of cells treated with said compound, e.g., a GATA3 inhibitor, into the system of the animal. When a compound of the disclosure or prodrug thereof is provided in combination with one or more other active agents, "administration" and its variants are each understood to include concurrent and sequential introduction of the compound or prodrug thereof and other agents or elements.

As used herein, "adipogenesis" is the formation of fat cells (adipocytes) from stem cells in an individual.

As used herein, "adipogenic capacity" measures the potential of preadipocytes found in adipose tissue to differentiate into adipocytes.

DNAzymes, also known as DNA enzymes, or catalytic DNA, refer to DNA oligonucleotides that are capable of performing a specific chemical reaction, often but not always catalytic.

"Insulin sensitivity" describes how sensitive the body is to the effects of insulin. Someone said to be insulin sensitive will require smaller amounts of insulin to lower blood glucose levels than someone who has low sensitivity.

"Insulin resistance" is an impaired, or reduced, response of the body to insulin, resulting in elevated levels of glucose in the blood (a key component of type 2 diabetes and metabolic syndrome).

The terms "pharmaceutical formulation" and "pharmaceutical composition" refer to preparations that are in such form as to permit the biological activity of the active ingredient to be effective, and that contain no additional components that are unacceptably toxic to an individual to which the formulation or composition would be administered. Such formulations or compositions may be sterile.

"Excipients" as used herein include pharmaceutically acceptable excipients, carriers, vehicles or stabilizers that are nontoxic to the cell or mammal exposed thereto at the dosages and concentrations employed. Often the physiologically acceptable excipient is an aqueous pH buffered solution.

Reference to a compound as described in a pharmaceutical composition, or to a compound as described in a claim to a pharmaceutical composition, refers to the compound described by the formula recited in the pharmaceutical composition, without the other elements of the pharmaceutical composition, that is, without carriers, excipients, etc.

As used herein, the terms individual, and patient are used interchangeably. The term "individual" refers to an animal, such as a mammal including a non-primate (e.g., a cow, pig, horse, cat, dog, rat or mouse) and a primate (e.g., a monkey such as a cynomolgous monkey, a chimpanzee and a human), and in certain embodiments, a human.

A "small molecule" as used herein refers to a compound of 1000 daltons or less in molecular weight.

GATA3 Inhibitors

GATA3 inhibitors that can be used in the embodiments disclosed herein include, but are not limited to, small molecules, antibodies, and antisense molecules including siRNA, ribozymes and deoxyribozymes (dnazymes).

Small molecule-based GATA3 inhibitors that may be used in embodiments describe herein include synthetic molecules as well as molecules isolated from naturally occurring compounds. For example, molecules displaying GATA3 inhibitory activity, e.g., such as *Holotrichia diomphalia* can be used. Pyrrothiogatain ((2,5-Dimethyl-1H-pyrrol-1-yl) thiophene-2-carboxylic acid) has also been shown to act as a GATA3 inhibitor (Nomura et al., *Scientific Reports*, 9: 17335 (2019)) and may be used in embodiments described herein. Corticosteroids may also be used to inhibit GATA3 in the compositions and methods described herein.

Anti-GATA3 antibodies, as exemplified but not limited to those as described in U.S. Pat. No. 9,429,577, are also used in some compositions and methods described herein. Anti-GATA3 polyclonal and anti-GATA3 monoclonal antibodies can be used in the compositions and methods described herein.

siRNA-based nucleic acids with GATA3 inhibitory activity as exemplified, by, but not limited to WO2019217423 may be used in compositions and methods as described herein.

DNAzymes (also known as deoxyribozymes, DNA enzymes, catalytic DNA, or DZ) can also be used as GATA3 inhibitors. For example, dnazymes with GATA3 inhibitory activity, as exemplified, but not limited to those as disclosed in U.S. Pat. Nos. 8,119,789, 9,249,413, 9,404,110, 9,428, 576, 9,417,243, U.S. Ser. No. 10/273,526, U.S. Ser. No. 10/487,325, and US20200131267 may be used in compositions and methods as described herein. In some embodiments, compositions comprising more than one dnazyme with GATA3 inhibitory activity is used. For example, the dnazyme hgd40 (5'-GTGGATGGAGGCTAGCTA-CAACGAGTCTTGGAG-3') (SEQ ID NO:1) can be used in methods and compositions described herein. Table 1 below provides other dnazymes that can be used in the methods and compositions described herein.

TABLE 1

| Dnazyme sequence | Sequence identifier |
|---|---|
| GTGGATGGAGGCTAGCTACAACGAGTCTTGGAG | 1 |
| TCACGGCAAGGCTAGCTACAACGAGAACTGGGT | 2 |
| TCGGTCAGAggctagctacaacgaTGCGTTGCT | 3 |
| GGCGTACGAggctagctacaacgaCTGCTCGGT | 4 |
| GGCGGCGTAggctagctacaacgaGACCTGCTC | 5 |
| CTCGGGTCAggctagctacaacgaCTGGGTAGC | 6 |
| TCCTCTGCAggctagctacaacgaCGGGGTCCT | 7 |
| ACTCTGCAAggctagctacaacgaTCTGCGAGC | 8 |
| GGGCGACGAggctagctacaacgaTCTGCAATT | 9 |
| AAGGGGCGAggctagctacaacgaGACTCTGCA | 10 |
| AAAACGGGAggctagctacaacgaCAGGTTGTA | 11 |
| AGAATAAAAggctagctacaacgaGGGACCAGG | 12 |
| ATGGCAGAAggctagctacaacgaAAAACGGGA | 13 |
| ATCCAAAAAggctagctacaacgaTGGGTATGG | 14 |
| AGGGGAAGAggctagctacaacgaAAAAATCCA | 15 |
| TTTTAAAAAggctagctacaacgaTATCTTGGA | 16 |
| GTGGGGGGAggctagctacaacgaGGGAAGGCT | 17 |
| GTTGAATGAggctagctacaacgaTTGCTTTCG | 18 |
| GTCGTTGAAggctagctacaacgaGATTTGCTT | 19 |
| GGCCCGGAAggctagctacaacgaCCGCGCGCG | 20 |
| TCACCTCCAggctagctacaacgaGGGCCTCGGC | 21 |
| CCGCCGTCAggctagctacaacgaCTCCATGGC | 22 |
| GGTGGCTCAggctagctacaacgaCCAGCGCGG | 23 |
| CGTTGAGCAggctagctacaacgaGGCGGGGTG | 24 |
| CCGCGTCCAggctagctacaacgaGTAGGAGTG | 25 |
| CAGCGGGTAggctagctacaacgaTGCGCCGCG | 26 |
| GCACATCCAggctagctacaacgaCTCCTCCGG | 27 |
| AAAAGCACAggctagctacaacgaCCACCTCCT | 28 |
| TAAAAAGCAggctagctacaacgaATCCACCTC | 29 |
| GACCGTCGAggctagctacaacgaGTTAAAAAG | 30 |
| TTGCCTTGAggctagctacaacgaCGTCGATGT | 31 |
| AGGGCGGGAggctagctacaacgaGTGGTTGCC | 32 |
| TGGCCCTGAggctagctacaacgaCGAGTTTCC | 33 |
| ACCTCTGCAggctagctacaacgaCGTGGCCCT | 34 |
| CGGAGGGTAggctagctacaacgaCTCTGCACC | 35 |
| GGCGGCACAggctagctacaacgaCTGGCTCCC | 36 |
| CGGGCGGCAggctagctacaacgaACCTGGCTC | 37 |

TABLE 1-continued

| Dnazyme sequence | Sequence identifier |
|---|---|
| AGGGATCCAggctagctacaacgaGAAGCAGAG | 38 |
| GGGTAGGGAggctagctacaacgaCCATGAAGC | 39 |
| GGGCTGAGAggctagctacaacgaTCCAGGGGG | 40 |
| GTGGATGGAggctagctacaacgaGTCTTGGAG | 41 |
| CGTGGTGGAggctagctacaacgaGGACGTCTT | 42 |
| GGGGGTAGAggctagctacaacgaGGAGAGGGG | 43 |
| GGAGGAGGAggctagctacaacgaGAGGCCGGG | 44 |
| GCCCCCCGAggctagctacaacgaAAGGAGGAG | 45 |
| CCGGGGAGAggctagctacaacgaGTCCTTCGG | 46 |
| GGACAGCGAggctagctacaacgaGGGTCCGGG | 47 |
| TGGGGTGGAggctagctacaacgaAGCGATGGG | 48 |
| CTTGAGGCAggctagctacaacgaTCTTTCTCG | 49 |
| CACCTGGTAggctagctacaacgaTTGAGGCAC | 50 |
| GCAGGGGCAggctagctacaacgaCTGGTACTT | 51 |
| CCAGCTTCAggctagctacaacgaGCTGTCGGG | 52 |
| GTGGGACGAggctagctacaacgaTCCAGCTTC | 53 |
| GGAGTGGGAggctagctacaacgaGACTCCAGC | 54 |
| ATGCTGCCAggctagctacaacgaGGGAGTGGG | 55 |
| GGGCGGTCAggctagctacaacgaGCTGCCACG | 56 |
| GAGGCTCCAggctagctacaacgaCCAGGGCGG | 57 |
| GTGGGTCGAggctagctacaacgaGAGGAGGCT | 58 |
| AGGTGGTGAggctagctacaacgaGGGGTGGTG | 59 |
| TGGCTTCTAggctagctacaacgaGCCCTCGTC | 60 |
| GGGCTCTGAggctagctacaacgaGCCTGGCTT | 61 |
| GGGACCCCAggctagctacaacgaCGGAGCCCG | 62 |
| GGTGGGGGAggctagctacaacgaCCCACCGGA | 63 |
| GGGGGGGGAggctagctacaacgaCCGAGGGCC | 64 |
| GGGCTGGGAggctagctacaacgaGGGCAGGGA | 65 |
| CGTCGAGGAggctagctacaacgaCCGCCCCTC | 66 |
| GGGCTGGCAggctagctacaacgaCTTCCCGTA | 67 |
| CGATGCCCAggctagctacaacgaCCGGGGCGG | 68 |
| GCTCCACGAggctagctacaacgaGCCCATCCG | 69 |
| CCGGCTCCAggctagctacaacgaGATGCCCAT | 70 |
| TCTCCGCAAggctagctacaacgaCCGGCTCCA | 71 |
| CCGTCAGCAggctagctacaacgaGTCTCCGCA | 72 |
| TCCCCGGCAggctagctacaacgaCGGCTCGGT | 73 |
| ACTCGGGCAggctagctacaacgaGTAGGGGGG | 74 |
| GGAGCTGTAggctagctacaacgaTCGGGCACG | 75 |

TABLE 1-continued

| Dnazyme sequence | Sequence identifier |
|---|---|
| GGACTTGCAggctagctacaacgaCCGAAGCCG | 76 |
| GGGCCTGGAggctagctacaacgaTTGCATCCG | 77 |
| TGTGCTGGAggctagctacaacgaCGGGCCTTG | 78 |
| GTTCACACAggctagctacaacgaTCCCTGCCT | 79 |
| CAGTTCACAggctagctacaacgaACTCCCTGC | 80 |
| CACAGTTCAggctagctacaacgaACACTCCCT | 81 |
| GTTGCCCCAggctagctacaacgaAGTTCACAC | 82 |
| TCGCCGCCAggctagctacaacgaAGTGGGGTC | 83 |
| CCCGTGCCAggctagctacaacgaCTCGCCGCC | 84 |
| GGCGTTGCAggctagctacaacgaAGGTAGTGT | 85 |
| TGGCTTCTAggctagctacaacgaGCCCTCGTC | 86 |
| CCCCCGCGAggctagctacaacgaGCTCGTCCG | 87 |
| GTAGGGAGAggctagctacaacgaCCCAGGCTG | 88 |
| GGGCGGGCAggctagctacaacgaCAAGGCGCC | 89 |
| CGGGAAGGAggctagctacaacgaTCGCCCGCG | 90 |
| TAGTCCTCAggctagctacaacgaGCGGCCCCG | 91 |
| TCCCCGACAggctagctacaacgaCTCCAGTCC | 92 |
| TTTCCCCGAggctagctacaacgaACCTCCAGT | 93 |
| TGAGCGCGAggctagctacaacgaCCTCAGTTT- | 94 |
| GGACCACAAggctagctacaacgaAGGTGGTTG | 95 |
| CTTGGACCAggctagctacaacgaAACAGGTGG | 96 |
| AAACTTGGAggctagctacaacgaCACAACAGG | 97 |
| CTGATTAAAggctagctacaacgaTTGGACCAC | 98 |
| TGGTGCTGAggctagctacaacgaTAAACTTGG | 99 |
| TGATGATCAggctagctacaacgaCTCTGTCTG | 100 |
| TGGTGATGAggctagctacaacgaCATCTCTGT | 101 |
| GCTTGGTGAggctagctacaacgaGATCATCTC | 102 |
| ATGGGAACAggctagctacaacgaCCGCCGTCC | 103 |
| GAATGGGAAggctagctacaacgaATCCGCCGT | 104 |
| TGACAGGAAggctagctacaacgaGGGAACATC | 105 |
| AGTAAATGAggctagctacaacgaAGGAATGGG | 106 |
| CACAGTAAAggctagctacaacgaGACAGGAAT | 107 |
| GCCCGGCCAggctagctacaacgaAGTAAATGA | 108 |
| CCACAAACAggctagctacaacgaCCTGTAGTG | 109 |
| GTCCACAAAggctagctacaacgaATCCTGTAG | 110 |
| CCACGTCCAggctagctacaacgaAAACATCCT | 111 |
| CCAAGACCAggctagctacaacgaGTCCACAAA | 112 |
| CCACCAAGAggctagctacaacgaCACGTCCAC | 113 |
| GCTGGTCCAggctagctacaacgaCAAGACCAC | 114 |
| GCTCTGGTAggctagctacaacgaCGCCAGTGG | 115 |
| CTGCACCCAggctagctacaacgaTTGCCGCTC | 116 |
| CACACTGCAggctagctacaacgaCCACTTGCC | 117 |
| CTTTCCACAggctagctacaacgaTGCACCCAC | 118 |
| GCCTTTCCAggctagctacaacgaACTGCACCC | 119 |
| TTCCTGGCAggctagctacaacgaGCTGCCCTC | 120 |
| GTGGACGTAggctagctacaacgaAGGCGGTTT | 121 |
| CCGGGTGGAggctagctacaacgaGTACAGGCG | 122 |
| CCTGGCGCAggctagctacaacgaCCAGTGCGC | 123 |
| CAAATGAAAggctagctacaacgaTTCCTGGCG | 124 |
| TTTCCCAAAggctagctacaacgaGAAACTTCC | 125 |
| ATTGTTGGAggctagctacaacgaGCCCCCTTG | 126 |
| TGGGTCACAggctagctacaacgaTGTTGGACG | 127 |
| TCTGGGTCAggctagctacaacgaATTGTTGGA | 128 |
| GCACAATCAggctagctacaacgaCTGGGTCAC | 129 |
| GGAGCACAAggctagctacaacgaCATCTGGGT | 130 |
| ACTGGAGCAggctagctacaacgaAATCATCTG | 131 |
| ATGGAGGGAggctagctacaacgaTGGAGCACA | 132 |
| TGGTACTTAggctagctacaacgaGGAGGGACT | 133 |
| GGGCTGGTAggctagctacaacgaTTATGGAGG | 134 |
| TCAACGATAggctagctacaacgaGCAGCCGGG | 135 |
| CCTCAACGAggctagctacaacgaATGCAGCCG | 136 |
| TCACCTCAAggctagctacaacgaGATATGCAG | 137 |
| CGTCGTTCAggctagctacaacgaCTCAACGAT | 138 |
| GTAAAGATAggctagctacaacgaGCGTGTTGG | 139 |
| AAGTAAAGAggctagctacaacgaATGCGTGTT | 140 |
| GGCAATGAAggctagctacaacgaTGGGTTTCT | 141 |
| TCACGGCAAggctagctacaacgaGAACTGGGT | 142 |
| AGGCAGTCAggctagctacaacgaGGCAATGAA | 143 |
| ATCTCGGCAggctagctacaacgaTCTGGTAGG | 144 |
| GCTGAGTAAggctagctacaacgaCTCGGCATT | 145 |
| TATTATCAAggctagctacaacgaTTTCAGCTG | 146 |
| GGGTTATTAggctagctacaacgaCAATTTTCA | 147 |
| AAGGGGTTAggctagctacaacgaTATCAATTT | 148 |
| CTCCCGGAAggctagctacaacgaCCTTTGGCA | 149 |
| GTACATGGAggctagctacaacgaTCAAAGTTC | 150 |
| AACTGGGTAggctagctacaacgaGGCAGAATA | 151 |

Dnazymes as used herein can be conjugated to a carrier molecule for stability or targeting purposes. Nanoparticles, micelles, liposomes, polymer complexes, may be used to increase in vivo stability of the dnazyme(s). For example, gold nanoparticles may be conjugated to dnazymes as described herein. In some embodiments, the nanoparticles are further complexed to a targeting moiety, e.g., such as an antibody, monoclonal antibody, targeting molecule, or ligand for a receptor on the target cell(s) or tissue. In some embodiments, the dnazyme is conjugated to a targeting moiety via a linker.

In some embodiments, non-naturally occurring dnazymes are synthesized and screened for GATA3 inhibitory activity in vitro using established methods as described, e.g., in U.S. Pat. No. 9,797,888.

Methods of Treatment

Some embodiments herein are directed to the use of a therapeutic agent comprising one or more GATA3 inhibitors for the treatment of insulin resistance, or related disorders or diseases, including, but not limited to obesity, hypertension, dyslipidemia and type 2 diabetes in an individual that has been diagnosed as having insulin resistance or Type II diabetes. Some embodiments are directed to the restoration of insulin sensitivity by administrating one or more GATA3 inhibitors.

Some embodiments herein are directed to the use of a therapeutic agent or pharmaceutical formulation comprising one or more GATA3 inhibitors to reverse, delay or prevent onset of insulin resistance or Type II diabetes in an individual that is at risk for developing insulin resistance or Type II diabetes. Some embodiments are directed to the administration of a pharmaceutical formulation comprising one or more GATA3 inhibitors to reduce risk of developing type II diabetes in an individual. In some embodiments, GATA3 inhibitors are administered to reduce or eliminate the phenotypical and/or metabolic symptoms characteristic of insulin resistance or a disorder or disease associated with it.

In other embodiments, an agent comprising one or more GATA3 inhibitors is administered locally to a tissue, or a site adjacent to said tissue, in order to increase the adipogenic capacity in said tissue. In some embodiments, localized exposure to a composition comprising a GATA3 inhibitor results in a decrease in GATA3 levels in said tissue. In some embodiments the administration of the GATA3 inhibitor(s) will result in an increase in adipogenesis in said tissue, thereby locally increasing fat deposits. In some embodiments, application of one or more GATA3 inhibitors locally results in a conversion of stem cells or preadipocytes into adipocytes at the site of application or adjacent tissues. In some embodiments, localized exposure to a formulation comprising a GATA3 inhibitor results in an increase in the number or % of adipocytes in said tissue.

In some embodiments, exposure to an effective amount of a composition comprising one or more GATA3 inhibitor(s) results in a decrease in adipocyte volume in visceral fat deposits and an increase in adipocyte volume in subcutaneous fat deposits.

In some embodiments, the administration of the GATA3 inhibitor(s) for stimulation of conversion of stem cells or preadipocytes into adipocytes is to achieve a desired cosmetic effect. In some embodiments a cosmetically effective amount of the GATA3 is administered to an individual. In some embodiments, inhibition of GATA3 in a tissue results in increased levels of adipocytes in subcutaneous tissues with low levels of adipocytes. In some embodiments, the increased levels of adipocytes in a tissue are a result of GATA3 inhibition-based adipogenesis. In some embodiments, cosmetic formulations comprising one or more GATA3 inhibitors are administered at or adjacent to the breast(s), thigh(s) or buttock(s) in order to stimulate adipogenesis is in said thighs or buttocks. In some embodiments, cosmetic formulations comprising one or more GATA3 inhibitors are applied to the skin of the extremities or to the subcutaneous tissue of the extremities in order to increase adipogenesis in said subcutaneous tissues of the extremities. In some embodiments the extremities are the hands or feet. In other embodiments, formulations comprising one or more GATA3 inhibitors are administered to the subcutaneous tissues in the backs of the hands, or neck to stimulate adipogenesis in said subcutaneous tissues to alleviate fat loss in those areas due to aging or weight loss.

Patients

In some embodiments, pharmaceutical formulations comprising one or more GATA3 inhibitors are administered to individuals suffering a metabolic disorder selected from the group consisting of elevated blood glucose (e.g., reduced ability to normalize glucose), impaired glucose tolerance, insulin resistance, type II diabetes, obesity, elevated percent body fat, and fatty liver (hepatic steatosis). Said individuals may be treated by the compositions and methods described herein. In some embodiments, the individual is a mammal. In some embodiments, the mammal is a human.

In other embodiments, individuals can be administered a composition comprising a GATA3 inhibitor for cosmetic purposes, i.e., a cosmetically effective amount of a composition comprising one or more GATA3 inhibitors to stimulate adipogenesis or to stimulate fat accumulation in a localized area. In some embodiments, the individual is a mammal. In some embodiments, the mammal is a human.

In some embodiments, patients are administered a GATA3 inhibitor in order to stimulate fat redistribution from a visceral deposit in the individual to a subcutaneous deposit in the thigh(s), buttock(s), extremities, neck, chest or face. In some embodiments the individual is a mammal. In some embodiments the mammal is a human.

In some embodiments, the visceral fat deposit is adjacent to the liver, stomach, or intestines. In some embodiments, the visceral fat deposit is the omentum.

Dosage Forms

In some embodiments described herein, the pharmaceutical compositions comprising a GATA3 inhibitor may be admixed with any suitable binder(s), lubricant(s), suspending agent(s), coating agent(s), solubilizing agent(s), and combinations thereof.

Solid oral dosage forms of pharmaceutical compositions, such as, tablets or capsules, comprising for example, dnazyme-based GATA3 inhibitors, can be administered in at least one dosage form at a time, as appropriate. These compositions can further contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). In some embodiments, the GATA3 inhibitor based pharmaceutical composition is in a sustained release or extended release formulation. Additional oral forms in which the present inventive compounds may be administered include elixirs, solutions, syrups, and suspensions; each optionally containing flavoring agents and coloring agents.

Alternatively, compositions as described herein can be administered by inhalation (intratracheal or intranasal) or in the form of a suppository or pessary.

In some embodiments, the therapeutic, pharmaceutical, or cosmetic formulations comprising one or more GATA3 inhibitors are formulated for topical application and are in the form of a lotion, solution, cream, ointment or dusting powder.

Creams comprising one or more GATA3 inhibitors as active ingredients can comprise a three phase system of an aqueous, an oily, and an emulsifying phase. In some embodiments, the emulsion of oil and water is in approximately equal proportions. Additionally, certain embodiments are directed to "augmented" creams, meaning they are more potent and penetrate the skin deeper. In some embodiments, creams comprising one or more GATA3 inhibitors can further comprise one or more cosmetically and/or pharmaceutically acceptable emulsifying agents, penetrating agent, permeation enhancers, active agent carriers and preservatives.

For topical administration, some embodiments can comprise, for example, gels and solutions, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In the preferred embodiment, the pharmaceutically acceptable carrier is a liposome or a biodegradable polymer.

Transdermal delivery systems further include patches, gels, tapes and creams, and can contain excipients such as solubilizers, permeation enhancers (e.g., fatty adds, fatty acid esters, fatty alcohols and amino acids), hydrophilic polymers (e.g., polycarbophil and polyvinylpyrolidone), and adhesives and tackifiers (e.g., polyisobutylenes, silicone-based adhesives, acrylates and polybutene). GATA3 inhibitors can be incorporated at a concentration of between about 0.01% and about 10% by weight, between about 0.05% and 10% by weight, between about 0.1 and about 10% by weight, between about 0.5% and about 10% by weight, between about 1 and about 10% by weight of the pharmaceutical formulation. In a preferred embodiment, said GATA3 inhibitors are encased in liposomes for delivery through the skin into the subcutaneous tissue. For example, the pharmaceutical composition can further cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, subcutaneously, intracavernosally, intravenously, intramuscularly, subcutaneously, intradermally, or intrathecally. In some embodiments, the compositions will also include at least one of a suitable carrier, a suitable excipient, and a suitable diluent.

In some embodiments described herein, the GATA3 inhibitors are bound or linked to a carrier for more efficient delivery of the inhibitor to the target tissue(s) or cells(s). GATA3 inhibitors as described herein can be bound to nanoparticles, micelles, or liposomes to improve specificity of delivery, or increase durability of said inhibitor in the body.

For parenteral administration, the pharmaceutical compositions of some embodiments are best used in the form of a sterile aqueous solution that may contain other substances, for example, enough salts and monosaccharides to make the solution isotonic with the tissue into which it is administered.

For buccal or sublingual administration, some embodiments as described herein may be administered in the form of tablets or lozenges, which can be formulated in a conventional manner.

In embodiments comprising topical administration of a GATA3 inhibitor comprising one or more molecules greater than 1000 daltons in size, such as one or more siRNAs, dnazymes, or antibodies, said administration can be done using microneedling, microporation, electroporation, iontophoresis, sonophoresis, or via passive administration using polymeric nanoparticles, liposomes, peptides, dendrimers or other carrier agents.

Therapeutic Dosage

Some embodiments are directed to methods of treating insulin resistance or a related disease or disorder in an individual by administration of a composition comprising one or more dnazymes with GATA3 inhibitory activity, wherein the dnazyme(s) are at a concentration between 1 ng/kg-10 mg/kg body weight, between 1 μg-10 mg/kg body weight, between 100 μg-10 mg/kg body weight, between 1 mg-10 mg/kg body weight, between 2.5 ng/kg-10 mg/kg body weight, between 2.5 μg-10 mg/kg body weight, between 250 μg-10 mg/kg body weight, between 2.5 mg-10 mg/kg body weight, between 5 ng/kg-10 mg/kg body weight, between 5 μg-10 mg/kg body weight, between 50 μg-10 mg/kg body weight, or between 500 or between 1 mg-10 mg/kg body weight.

Some embodiments are directed to methods of treating insulin resistance or a related disease or disorder in an individual by administration of a composition comprising one or more dnazymes with GATA3 inhibitory activity, wherein the dnazyme(s) are at a concentration in the range of between 0.01 and 10%, between 0.1 and 10%, between 1 and 10%, between 0.05 and 10%, between 0.1 and 10%, between 0.05 and 10%, between 0.0025 and 10%, between 0.025 and 10%, between 0.25 and 10%, between 2.50 and 10%, between 0.01 and 0.05%, between 0.01 and 0.5%, or between 0.01 and 5% of said composition.

Some embodiments described herein are directed to treatment regiments wherein said therapeutic composition is administered 1×, 2×, 3×, 4×, or 5× daily.

Cosmetic Dosage

Some embodiments are directed to cosmetic methods for inducing adipogenesis in an individual by administration of a composition comprising one or more dnazymes with GATA3 inhibitory activity. In some embodiments the cosmetic composition is a cream, gel or ointment. In some embodiments the composition comprises dnazyme(s) with GATA3-inhibitory activity at a concentration in the range of between 0.01 and 10%, between 0.1 and 10%, between 1 and 10%, 0.01 and 10%, between 0.1 and 10%, between 1 and 10%, between 0.0025 and 10%, between 0.025 and 10%, between 0.25 and 10%, between 2.50 and 10%, between 0.01 and 0.05%, between 0.01 and 0.5%, or between 0.01 and 5% of said cosmetic composition.

Those embodiments directed to methods for effecting adipogenesis in target tissues, e.g., in the subcutaneous fat deposits of breast(s), thigh(s), and buttock(s), may require one or more physically invasive procedures comprising microneedling, microporation, electroporation, iontophoresis, or sonophoresis to achieve the desired results, i.e., increasing the size of fat deposits in said tissues.

In those embodiments using passive methods to deliver the GATA3 inhibitor(s) of the invention to target tissues, application of cosmetic compositions comprising the GATA3 inhibitor(s) and carrier agents may require repeated application. For example, passive administration of the GATA3 inhibitors for cosmetic purposes may require daily, semi-daily, weekly, or semiweekly for a period of between 1 day and 1 year.

Combination Therapy

Some embodiments are directed to the use of one or more GATA3 inhibitors in combination therapy for the treatment of insulin resistance. For example, GATA3 inhibitors of the invention may be administered simultaneously or sequentially with metabolic disease-based drugs including, but not limited to Metformin, Glucophage, Glucophage XR, Fortamet, Glumetza, Riomet), insulin, Humulin R, or Novolin R for the restoration of insulin sensitivity.

EXAMPLES

Example 1: Expression of Adipogenic Factors in Insulin Sensitive and Insulin Resistant Individuals Materials and Methods Cohort: Recruitment criteria of participants were previously described (Almuraikhy et al., *Diabetologia*, 59(11): 2406-2416 (2016)). Protocols were approved by the Institutional Review Board of ADLQ (X2017000224). Data from paired subcutaneous (SC) and omental (OM) adipose tissues from 10 consented obese females undergoing bariatric surgery at Al-Emadi hospital (Doha, Qatar) were used for this study. Insulin resistance was assessed by the homeostatic model assessment (HOMA-IR) (Grundy et al., *Arterioscler Thromb Vasc Biol.*, 24(2):e13-8 (2004)), using 30th percentile (HOMAIR=2.4) as a threshold point. Accordingly, subjects were dichotomized into IS (HOMA-IR<2.4, n=5 and IR (HOMA-IR>2.4, n=5).

Secreted cytokine profiling: Profiling of secreted cytokines from SC preadipocytes from 5-6 participants was performed using media supernatants collected following completion of differentiation. Accumulated levels of secreted IL-6 and IL-10 in the last 4 days before staining were measured using Inflammatory Cytokine Human Magnetic 5-Plex (Life Technologies) according to manufacturer's instructions and assessed by Luminex Flexmap 3D using xPONENT 4.2 software.

3T3L-1 cell culture and differentiation: Mouse 3T3L-1 preadipocytes were cultured in DMEM growth media (Gibco) supplemented with 10% heat-inactivated fetal bovine serum (Sigma) and 1% antibiotics (Gibco). After reaching confluency, cells were induced to differentiate (day 0) using a growth medium supplemented with 10 µg/ml insulin, 0.5 mM 1-methyl-3-isobutyl-xanthine (IBMX) and 1 µM dexamethasone. On day 3, the medium was changed to post-differentiation medium supplemented only with 10 µg/ml insulin until day 10. To induce insulin resistance, cells were differentiated in the presence of 10 µM of 4-hydroxynonenanl (4HNE) as previously described (Elkayress et al., *Free Radic. Biol. Med.* 104:129-137 (2017).

Targeting GATA3 expression: GATA3 mRNA specific DNAzyme sequence (hgd40: GTGGATGGAGGCTAGC-TACAACGAGTCTTGGAG)(SEQ ID NO:1) and the control scrambled DNAzyme sequence (ODNg: 5'-TGT-GATGTAGGCTAGCTACAACGACAGATGGAA)(SEQ ID NO:152) were obtained from Integrated DNA Technologies (IDT). 3T3L-1 cells, seeded in 24 well plate (42000 cells/well) one day before transfection, were transfected with DNAzyme complexed with Lipofectamine 3000 transfection reagent (Thermo Fisher Scientific) in Opti-MEM media (Gibco) with a final concentration of DNAzyme of 1 ng/µL according to manufacturer's instructions. Transfection was carried out for 6-8 hours followed by replacing media with adipogenic differentiation media.

Assessment of adipogenesis: At day 11, differentiated adipocytes were stained with oil red 0 (ORO) for assessment of adipogenesis as described previously (Krause et al., Adipocyte, (2016)). Briefly, differentiated cells were fixed with 4% paraformaldehyde for 15 minutes at room temperature, washed with 1×PBS and incubated with ORO working solution for 30 min at room temperature. The wells were then washed 5 times with water, followed by dye elution with 100% 2-propanol. The absorption of resulting color was measured using EPOCH2 microplate reader from BioTek at 510 nm according to manufacturer's instructions.

Western Blotting: Cells were washed once in PBS and lysed directly in RIPA lysis buffer (150 mM NaCl, 50 mM Tris pH 7.5, 0.1% SDS, 1 mM EDTA, 1 mM EGTA, 0.5% NaDoc (Sigma), 1% Triton X-100) supplemented with protease inhibitor cocktail (Sigma), 10 mM sodium fluoride (Sigma), 1 mM sodium orthovanadate (Sigma), 1 mM PMSF (Sigma), 5 mM benzamidine (Sigma), 20 µg/ml calpain inhibitor (Sigma), 5 mM nicotinamide (Sigma), and 3 mM trichostatin A (InvivoGen). Protein lysates were homogenized by a sonicator, centrifuged at 15,000 g for 10 min at 4° C. and supernatants were collected for protein estimation using DC Protein Assay (Bio-Rad) with CLAR-IOstar microplate reader (BMG LABTECH). 50-100 µg of whole-cell extracts per sample were separated on SDS-PAGE and transferred to PVDF membrane (Bio-Rad). The blots were probed with the following antibodies: GATA-3 (D13C9; Cell Signaling Technology, RRID: AB 2798212), GAPDH (14C10; Cell Signaling Technology, RRID: AB 561053). Signals were detected in the presence of Super-Signal™ West Dura Extended Duration Substrate (Thermo Fisher Scientific) using ChemiDoc™ MP imaging system (Biorad). Band intensities were quantified using ImageJ software.

Assessment of gene Expression: RNA from differentiated adipocytes was extracted using TRIzol method (Invitrogen) according to manufacturer's instructions. Three µg of the resulting RNA was used for First-strand cDNA synthesis using Superscript III first strand synthesis super mix kit (Invitrogen) according to manufacturer's instructions. Real-time PCR was carried out for gene expression analysis using ing of the produced cDNA with the primers listed in Table 2 using 7500 Real Time PCR System from Applied Biosystem. The PCR conditions were as follows: 1 cycle of 95° C. for 10 min, 45 cycles of 95° C. for 15 s, 55° C. for 40 s and 72° C. for 30 cycles and finally 60° C. for 15 s. Real-time PCR was carried out in triplicate and the GAPDH was used as a housekeeping gene for normalization of the amplified signals of the target genes. The data analysis was performed using the ΔΔCt based calculation. For measuring the effect of GATA3 inhibition on insulin resistance-related genes, RT$^2$ Profiler™ PCR Array Mouse Insulin Resistance (PAMNI-156Z) was used according to the manufacturer's protocol (QIAGEN). The array contains C-C chemokine receptor type 5 (Ccr5), Janus Kinase 2 (Jak2), caspase 1 (Casp1), Sterol regulatory element-binding transcription factor 1 (Srebf1), Glucuronidase beta (Gusb), C-C chemokine receptor type 4 (Ccr4), leptin receptor (Lepr) and Peroxisome proliferator-activated receptor alpha (Ppara). The PCR experiments were performed using QuantStudio 6 Flex from Applied Biosystem and data analyzed using the ΔΔCt-based calculations.

TABLE 2

A list of primers sequence.

| Gene | Primers sequences (5' to 3') | SEQ ID NO: |
|---|---|---|
| GATA3 | f: GAACCGGCCCCTTATCAAG | 153 |
| | r: ACAGTTCGCGCAGGATGTC | 154 |

TABLE 2-continued

A list of primers sequence.

| Gene | Primers sequences (5' to 3') | SEQ ID NO: |
|---|---|---|
| GAPDH | f: AGGTCGGTGTGAACGGATTTG | 155 |
| | r: TGTAGACCATGTAGTTGAGGTCA | 156 |
| IL-6 | f: TAGTCCTTCCTACCCCAATTTCC | 157 |
| | r: TTGGTCCTTAGCCACTCCTTC | 158 |
| IL-10 | f: GCTCTTACTGACTGGCATGAG | 159 |
| | r: CGCAGCTCTAGGAGCATGTG | 160 | f: forward, r: reverse, GATA3: GATA binding protein 3, GAPDH: Glyceraldehyde 3-phosphate dehydrogenase, IL6: interleukin 6 and IL10: interleukin 10.

Insulin signaling analysis: The effect of GATA3 inhibition on insulin resistance biomarkers was quantified in equal volumes of lysates prepared from GATA3 DNAzyme transfected 3T3L-1 cells using Bio-Plex Pro Mouse Diabetes 8-Plex Assay (171F7001M, BIO-RAD), following manufacturer's instructions and assessed by Luminex 200 using xPONENT 4.2 software.

Statistical analysis: T-test and Wilcoxon-Mann-Whitney test were performed as appropriate using IBM SPSS statistics 21 (Armonk, NY, USA). Non-parametric tests were used for comparing ordinal or non-normal variables. Significance was defined as $p \leq 0.05$.

Individuals were premenopausal (33.1±years of age) with a weight range of (43.9±5.2 Kg/m 2). Participants showed hypercholesterolemia (4.8±0.84 mM/L), hyperleptinemia (58±26 ng/ml) and hyperinsulinemia (10.6±5.4 mIU/L) and were dichotomized into IS and IR groups based on their HOMA-ITR index.

Insulin resistance was assessed by the homeostatic model assessment (HOMA-IR) ((Grundy et al., *Arterioscler Thromb Vasc Biol.*, 24(2):e13-8 (2004)) using $30^{th}$ percentile (HOMAIR=2.4) as a threshold point. Subjects were dichotomized into IS (HOMA-IR<2.4, n=5) and IR (HOMA-IR>2.4, n=5). Table 3 provides characteristics of the participant groups.

TABLE 3

| Variables | Cohort (n = 10) | IS (N = 5) | IR (N = 5) | p value |
|---|---|---|---|---|
| Age (year) | 33.1 (11.6) | 33.6 (13.1) | 29.8 (10.2) | 0.62 |
| BMI (kg · m$^{-2}$) | 44 (5.2) | 42.5 (2) | 44.8 (7.6) | 0.52 |
| SBP (mmHg) | 118.5 (13.5) | 121.2 (9.6) | 113.6 (17.2) | 0.41 |
| DBP (mmHg) | 67.7 (12.2) | 66.6 (14.0) | 68.00 (13) | 0.87 |
| MAP | 84.7 (12.1) | 84.8 (12.2) | 83.2 (12.3) | 0.86 |
| Cholesterol (mmol/L) | 4.8 (0.84) | 4.3 (0.92) | 5.1 (0.65) | 0.16 |
| LDL (mmol/L) | 2.9 (0.81) | 2.7 (1.03) | 3 (0.65) | 0.61 |
| Triglyceride (mmol/L) | 1.1 (0.35) | 1.01 (0.3) | 1.1 (0.44) | 0.69 |
| Triglyceride/HDL | 2.02 (1.3) | 2.4 (1.9) | 1.6 (0.73) | 0.4 |
| HDLC (mmol/L) | 1.4 (0.39) | 1.2 (0.35) | 1.6 (0.36) | 0.08 |
| Leptin (ng/ml) | 58 (26) | 60 (35) | 57.5 (22.2) | 0.9 |
| IL-6 (pg/ml) | 3.6 (2) | 3 (1.1) | 4.1 (2.5) | 0.34 |
| FBG (mmol/L) | 7.3 (4.4) | 5.2 (0.54) | 6.8 (2.6) | 0.24 |
| Insulin (mIU/L) | 10.6 (5.4) | 6.8 (4.3) | 13.8 (4.7) | 0.03 |
| HOMA-IR | 3.4 (2.4) | 1.6 (0.9) | 4 (1.4) | 0.009 |
| Albumin (g/L) | 42 (4.8) | 43.6 (4) | 41.7 (5) | 0.5 |
| ALP (IU/L) | 72 (22.3) | 83.2 (25.3) | 59.3 (14) | 0.078 |
| ALT (IU/L) | 27.1 (18.4) | 22.8 (8.6) | 31.2 (25.4) | 0.5 |
| AST (IU/L) | 20.8 (10.9) | 18.8 (3.4) | 23.7 (14.6) | 0.5 |
| Bilirubin (µmol/L) | 8.5 (3.6) | 10.8 (3) | 7.2 (3.4) | 0.1 |

Mediators of metabolic syndrome were measured in insulin sensitive (IS) and insulin resistant (IR) including body Profiling of secreted cytokines from SC preadipocytes from 5-6 participants was performed using media supernatants collected following completion of differentiation. Accumulated levels of secreted IL-6 and IL1β in the last 4 days before staining was assessed using Inflammatory Cytokine Human Magnetic 5-Plex (Life Technologies) according to manufacturer's instructions and assessed using Luminex Flexmap 3D using xPONENT 4.2 software.

Adipose tissue samples taken from insulin sensitive and insulin resistant individuals and mRNA levels were also assessed using RT-PCR using RT2 Profiler™ PCR Array Human Adipogenesis, Catalog No. PAHS-049Z(Qiagen).

Figure 2:
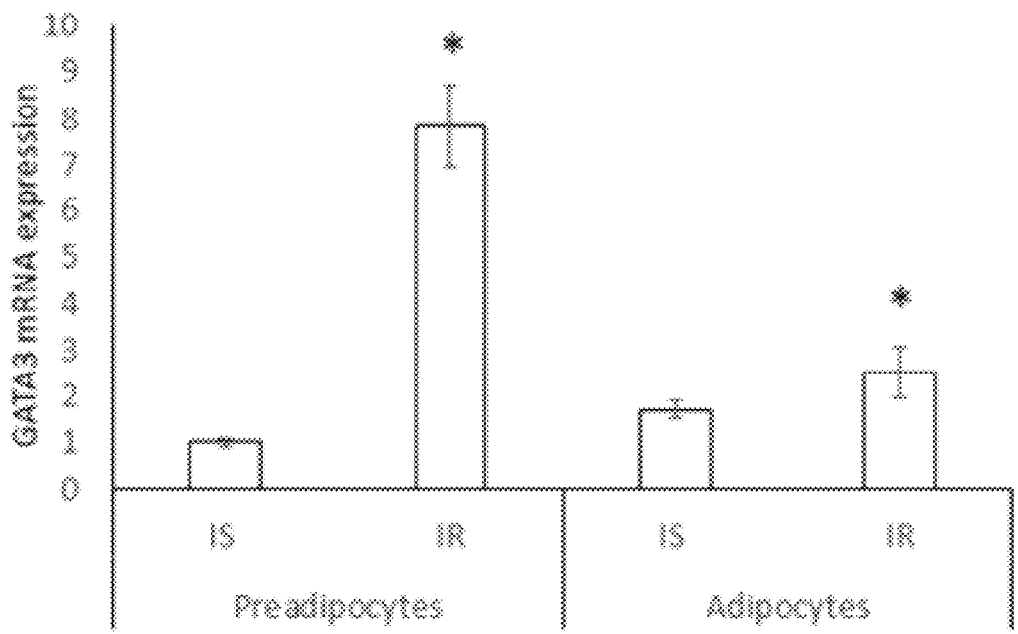
FIG. 2 shows GATA3 expression in expanded preadipocytes/adipocytes from SC tissues from insulin sensitive (IS) and insulin resistant (IR) individuals by RT-PCR in human adipose tissue from insulin sensitive (IS) and insulin resistant (IR) individuals.
Figure 3:
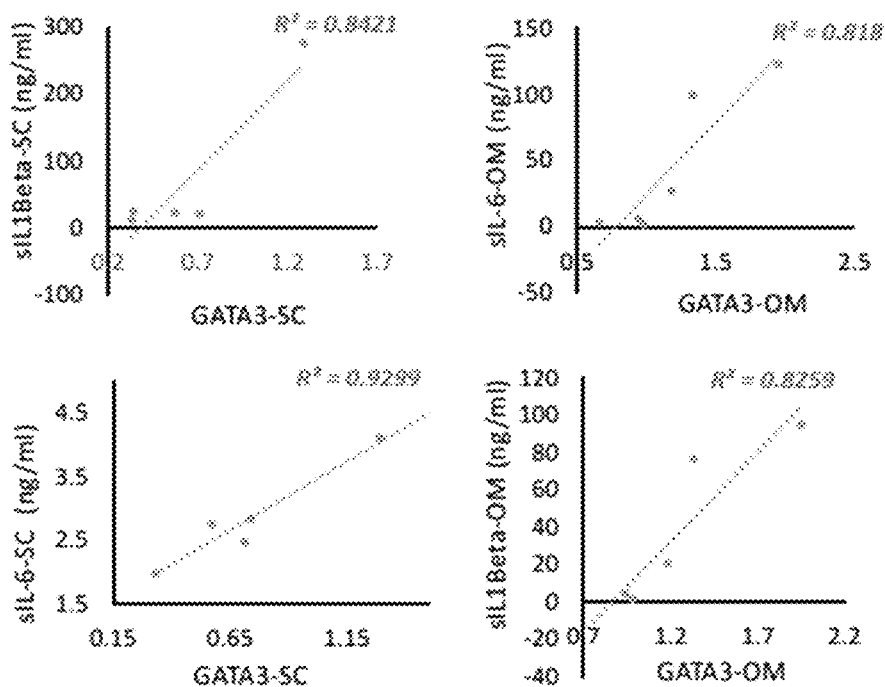
FIG. 3 shows the correlation between GATA3 mRNA of secreted inflammatory cytokines IL1f3, IL-6.

GATA-3 expression was quantified in SC and OM adipose tissues and in preadipocyte cultures expanded from SC adipose tissues from IS and IR individuals. Western blotting data indicated higher expression of GATA3 in OM compared to SC adipose tissues, regardless of the insulin resistance status of tissue donors (FIG. 1). RT-PCR results showed higher expression of GATA3 in preadipocytes and differentiating preadipocytes from IR obese individuals compared to IS counterparts (FIG. 2). Interestingly, there was a significant positive correlation between GATA3 expression and secreted IL-6 and IL-beta from SC and OM differentiated adipocytes as presented as mean±SEM. *P<0.05, paired and independent sample t-test. (FIG. 3).

Example 2: Effect of GATA3 Inhibition on 3T3L-1 Preadipocyte Adipogenic Differentiation To determine whether inhibition of GATA3 could affect the adipogenic capacity of murine 3T3L-1 cells in vitro, GATA3 expression was assessed following transfection with hgd40 DNAzyme targeting GATA3 mRNA in the presence or absence of the anti-adipogenic reactive aldehyde 4HNE.

Mouse 3T3L-1 preadipocytes were cultured in DMEM growth media (Gibco) supplemented with 10% heat-inactivated fetal bovine serum (Sigma) and 1% antibiotics (Gibco). After reaching confluency, cells were induced to differentiate (day 0) using a growth medium supplemented with 10 µg/ml insulin, 0.5 mM 1-methyl-3-isobutyl-xanthine (IBBMX) and 1 µM dexamethasone. On day 3, the medium was changed to post-differentiation medium supplemented only with 10 µg/ml insulin until day 10. To induce insulin resistance, cells were differentiated in the presence of 10 µM of 4-hydroxynonenanl (4HNE).

DNA sequences (hgd40: 5'-GTGGATGGAGGCTAGC-TACAACGAGTCTTGGAG)(SEQ ID NO:1) and the control scrambled DNAzyme sequence (ODNg: 5'-TGT-GATGTAGGCTAGCT-ACAACGACAGATGGAA)(SEQ ID NO:152) were obtained from Integrated DNA Technologies (IDT). 3T3L-1 cells, seeded in 24 well plate (42000 cells/well) one day before transfection, were transfected with DNAzyme complexed with Lipofectamine 3000 transfection reagent (Thermo Fisher Scientific) in Opti-MEM media (Gibco) with a final concentration of DNAzyme of 1 ng/µL according to manufacturer's instructions. Transfection was carried out for 6-8 hours followed by replacing media with adipogenic differentiation media.

Figure 4:
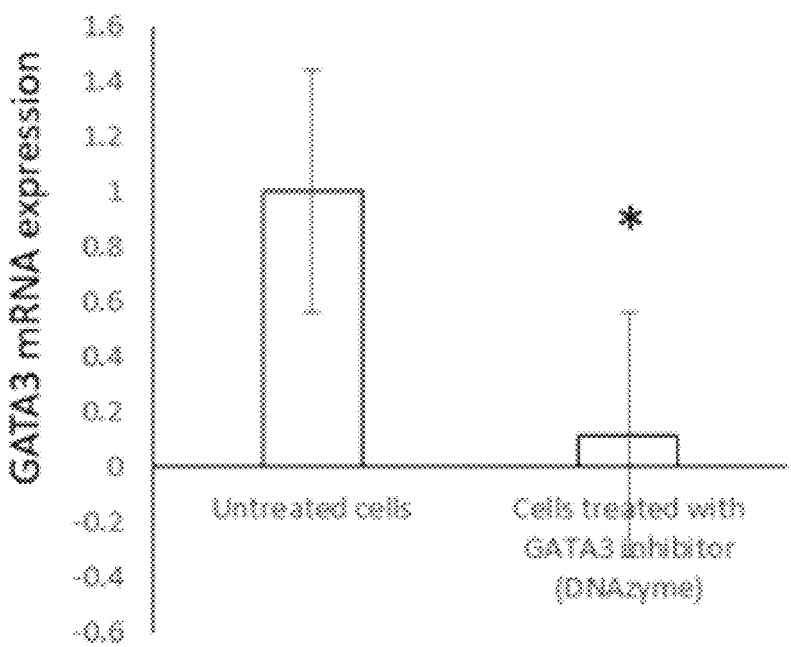
FIG. 4 shows the effect of a GATA3 inhibitor on GATA3 mRNA expression levels.
Figure 5:
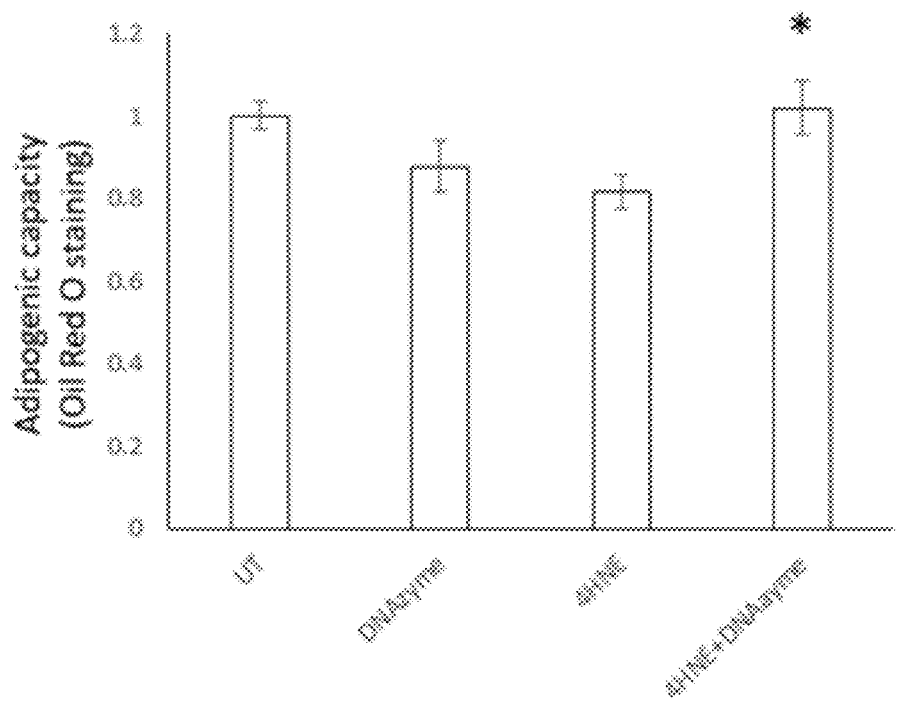
FIG. 5 shows the effect of 4HN treatment on preadipocytes differentiation.
Figure 6:
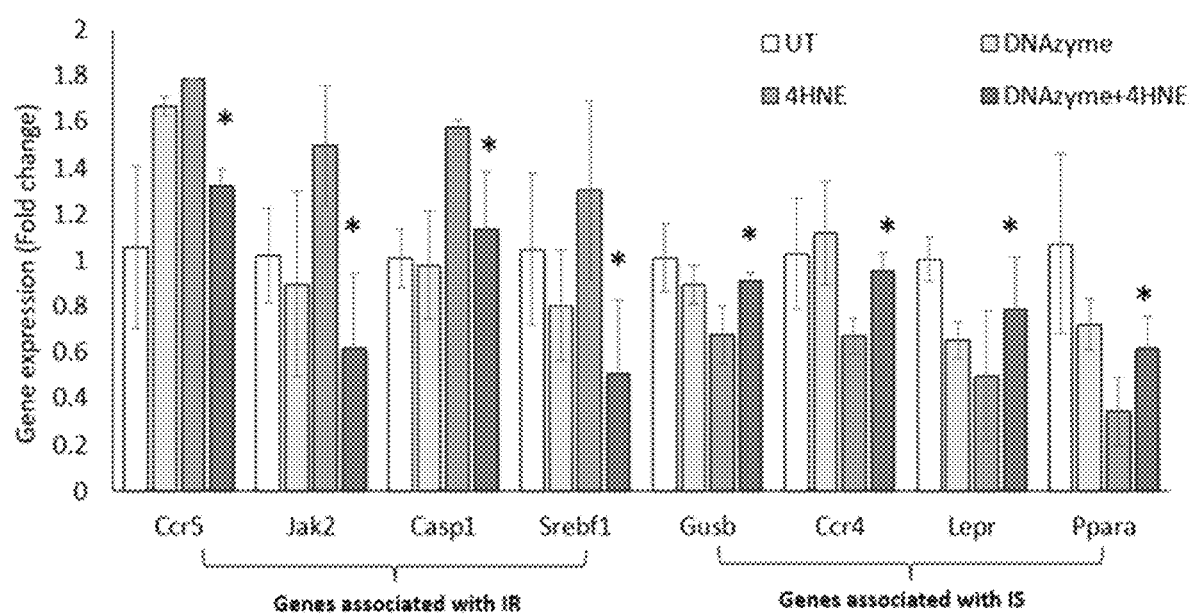
FIG. 6 shows compares relative mRNA expression levels of selected insulin signaling genes in mouse 3T3L1 cells in vitro.
Figure 8:
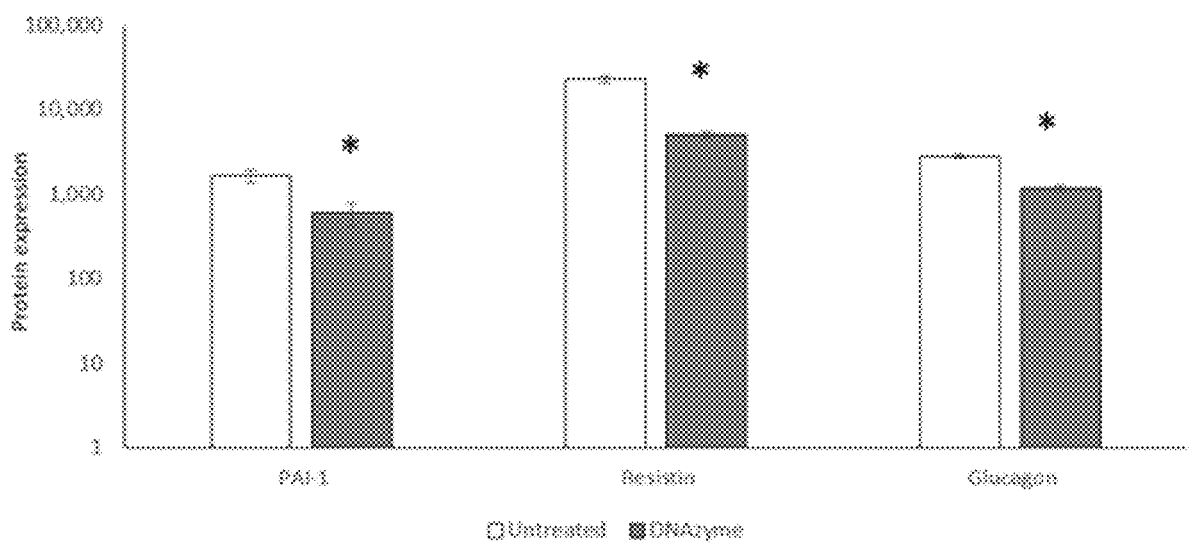
FIG. 8 shows the effect of a GATA3 inhibitor on insulin resistance-related biomarkers. *P<0.05, independent sample t-test.

GATA3 expression was down-regulated in differentiated adipocytes (FIG. 4), and triggered higher adipogenic capacity of 3T3L1 preadipocytes (FIG. 5). Additionally, co-treatment of 3T3L1 with the anti-adipogenic reactive aldehyde 4HNE and GATA3 inhibitor (hgd40) rescued adipogenesis compared with cells treated with 4HNE alone (FIG. 8). Additionally, co-treatment of cells with 4HNE and hgd40 improved their insulin sensitivity by increasing the expression of genes associated with insulin sensitivity, including Ccr4, Gusb, Lepr and Ppara, and decreasing the expression of genes associated with insulin resistance such as Jak2, Casp1, Srebf1 and Ccr5 (FIG. 6).

The superior adipogenic capacity in metabolically healthy obese (MHO) individuals MHO group is found to be mediated, at least in part, by lower levels of the inflammatory mediator interleukin-6 (IL-6) (Almuraikhy et al., *Diabeologia*, 59(11):2406-2416 (2016)), reactive aldehyde 4-hydroxynonenal (4-HNE) (Elrayess et al., *Free Radic Biol Med*, 104:129-137 (2017)), the environmental pollutants polybrominated diphenyl ethers (Helaleh et al., *Chemosphere*, 209:268-276 (2018)), and the combined treatment of metformin and insulin (Jaganjac et al., *Redox Biol*, 12:483-490 (2017) and Al-Sulaiti et al., Intech Open, DOI: 10.5772, (2019)). As seen in FIG. 3, lower panel, preadipocytes treated with the dnazyme-based GATA3 inhibitor had reversal of the reactive aldehyde 4-hydroxynonenal (4-HNE) induced impairment of adipogenesis in murine 3T3L1 cells as well as increased adipogenic capacity. As seen in FIG. 4, upper panel, treatment of primary 3T3L-1 mouse preadipocytes with the dnazyme-based GATA3 inhibitor showed similar results. FIGS. 3 and 6 show the correlation between GATA3 mRNA of secreted inflammatory cytokines IL1β, IL-6, and the correlation between GATA3 and circulating IL-6 protein levels, respectively.

Example 3: Effect of GAT-3 on Insulin Signaling Genes and Insulin Sensitivity

Figure 7:
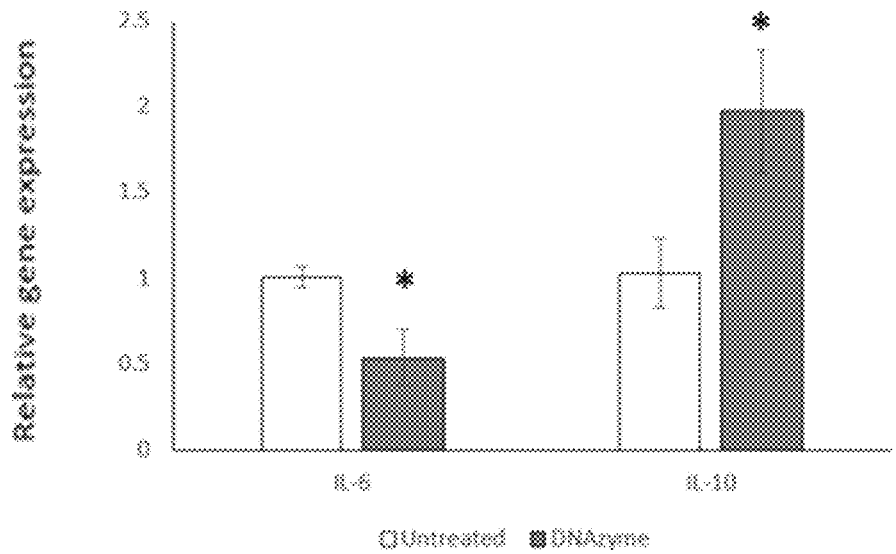
FIG. 7 shows the effect of a GATA3 inhibitor on inflammatory biomarkers. *P<0.05, independent sample t-test.

To investigate whether GATA3 expression affects inflammatory markers associated with obesity and insulin resistance, the impact of GATA3 inhibition on the expression of pro-inflammatory IL6 and anti-inflammatory IL10 was investigated. Results indicated a significant reduction in IL6 expression and an increase in IL10 expression following GATA3 inhibition (FIG. 7). Similarly, the effect of GATA3 inhibition on expression of insulin resistance-related proteins was assessed in 3T3L-1. Data indicated a significant reduction in PAI-1, resistin and glucagon in response to GATA3 inhibition (FIG. 8).

All referenced disclosed herein are incorporated by reference in their entirety.

The invention claimed is:

1. A method of reducing insulin resistance in an individual in need thereof by inhibiting GATA3 expression, wherein the GATA3 expression is inhibited by administering to the subject an effective amount of a dnazyme having an oligonucleotide sequence selected from any one of SEQ ID NOs: 1-151.

2. The method of claim 1, wherein the dnazyme is hgd40 having an oligonucleotide sequence of SEQ ID NO:1.

3. The method of claim 1, wherein the individual is a mammal.

4. The method of claim 3, wherein the mammal is a human.

5. The method of claim 4, wherein the human is suffering from insulin resistance or Type II diabetes.

6. The method of claim 1, wherein the administering of the GATA3 inhibitor to the subject comprises increasing expression of IL-10 gene and decreasing expression of IL-6, PAI-I, resistin, and glucagon genes in the subject.

7. A method of reducing impaired adipogenesis in a subject in need thereof by inhibiting GATA3 expression, wherein the GATA3 expression is inhibited by administering to the subject an effective amount of a dnazyme having an oligonucleotide sequence selected from any one of SEQ ID NOs: 1-151.

8. The method of claim 7, wherein the dnazyme is hgd40 having an oligonucleotide sequence of SEQ ID NO:1.

9. The method of claim 7, wherein the patient is a mammal.

10. The method of claim 9, wherein the mammal is a human.

* * * * *

SEQUENCE LISTING

```
Sequence total quantity: 160
SEQ ID NO: 1            moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 1
gtggatggag gctagctaca acgagtcttg gag                               33

SEQ ID NO: 2            moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 2
tcacggcaag gctagctaca acgagaactg ggt                               33

SEQ ID NO: 3            moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 3
tcggtcagag gctagctaca acgatgcgtt gct                               33
```

-continued

```
SEQ ID NO: 4              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 4
ggcgtacgag gctagctaca acgactgctc ggt                                33

SEQ ID NO: 5              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 5
ggcggcgtag gctagctaca acgagacctg ctc                                33

SEQ ID NO: 6              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 6
ctcgggtcag gctagctaca acgactgggt agc                                33

SEQ ID NO: 7              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 7
tcctctgcag gctagctaca acgacggggt cct                                33

SEQ ID NO: 8              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 8
actctgcaag gctagctaca acgatctgcg agc                                33

SEQ ID NO: 9              moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 9
gggcgacgag gctagctaca acgatctgca att                                33

SEQ ID NO: 10             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 10
aagggcgag gctagctaca acgagactct gca                                 33

SEQ ID NO: 11             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 11
```

```
aaaacgggag gctagctaca acgacaggtt gta                                  33

SEQ ID NO: 12            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 12
agaataaaag gctagctaca acgagggacc agg                                  33

SEQ ID NO: 13            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 13
atggcagaag gctagctaca acgaaaaacg gga                                  33

SEQ ID NO: 14            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 14
atccaaaaag gctagctaca acgatgggta tgg                                  33

SEQ ID NO: 15            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 15
agggaagag gctagctaca acgaaaaaat cca                                   33

SEQ ID NO: 16            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 16
ttttaaaaag gctagctaca acgatatctt gga                                  33

SEQ ID NO: 17            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 17
gtgggggag gctagctaca acgagggaag gct                                   33

SEQ ID NO: 18            moltype = DNA  length = 33
FEATURE                  Location/Qualifiers
misc_feature             1..33
                         note = Dnazyme
source                   1..33
                         mol_type = other DNA
                         organism = synthetic construct
SEQUENCE: 18
gttgaatgag gctagctaca acgattgctt tcg                                  33

SEQ ID NO: 19            moltype = DNA  length = 33
FEATURE                  Location/Qualifiers
misc_feature             1..33
                         note = Dnazyme
source                   1..33
                         mol_type = other DNA
                         organism = synthetic construct
```

```
SEQUENCE: 19
gtcgttgaag gctagctaca acgagatttg ctt                                   33

SEQ ID NO: 20           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 20
ggcccggaag gctagctaca acgaccgcgc gcg                                   33

SEQ ID NO: 21           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 21
tcacctccag gctagctaca acgaggcctc ggc                                   33

SEQ ID NO: 22           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 22
ccgccgtcag gctagctaca acgactccat ggc                                   33

SEQ ID NO: 23           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 23
ggtggctcag gctagctaca acgaccagcg cgg                                   33

SEQ ID NO: 24           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 24
cgttgagcag gctagctaca acgaggcggg gtg                                   33

SEQ ID NO: 25           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 25
ccgcgtccag gctagctaca acgagtagga gtg                                   33

SEQ ID NO: 26           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 26
cagcgggtag gctagctaca acgatgcgcc gcg                                   33

SEQ ID NO: 27           moltype = DNA  length = 33
FEATURE                 Location/Qualifiers
misc_feature            1..33
                        note = Dnazyme
source                  1..33
                        mol_type = other DNA
```

```
                        organism = synthetic construct
SEQUENCE: 27
gcacatccag gctagctaca acgactcctc cgg                                     33

SEQ ID NO: 28           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 28
aaaagcacag gctagctaca acgaccacct cct                                     33

SEQ ID NO: 29           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 29
taaaaagcag gctagctaca acgaatccac ctc                                     33

SEQ ID NO: 30           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 30
gaccgtcgag gctagctaca acgagttaaa aag                                     33

SEQ ID NO: 31           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 31
ttgccttgag gctagctaca acgacgtcga tgt                                     33

SEQ ID NO: 32           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 32
agggcgggag gctagctaca acgagtggtt gcc                                     33

SEQ ID NO: 33           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 33
tggccctgag gctagctaca acgacgagtt tcc                                     33

SEQ ID NO: 34           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 34
acctctgcag gctagctaca acgacgtggc cct                                     33

SEQ ID NO: 35           moltype = DNA   length = 33
FEATURE                 Location/Qualifiers
misc_feature            1..33
                        note = Dnazyme
source                  1..33
```

```
                           mol_type = other DNA
                           organism = synthetic construct
SEQUENCE: 35
cggagggtag gctagctaca acgactctgc acc                                 33

SEQ ID NO: 36              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 36
ggcggcacag gctagctaca acgactggct ccc                                 33

SEQ ID NO: 37              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 37
cgggcggcag gctagctaca acgaacctgg ctc                                 33

SEQ ID NO: 38              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 38
agggatccag gctagctaca acgagaagca gag                                 33

SEQ ID NO: 39              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 39
gggtagggag gctagctaca acgaccatga agc                                 33

SEQ ID NO: 40              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 40
gggctgagag gctagctaca acgatccagg ggg                                 33

SEQ ID NO: 41              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 41
gtggatggag gctagctaca acgagtcttg gag                                 33

SEQ ID NO: 42              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 42
cgtggtggag gctagctaca acgaggacgt ctt                                 33

SEQ ID NO: 43              moltype = DNA   length = 33
FEATURE                    Location/Qualifiers
misc_feature               1..33
                           note = Dnazyme
```

```
                          -continued source                  1..33
                        mol_type = other DNA
                        organism = synthetic construct
SEQUENCE: 43
gggggtagag gctagctaca acgaggagag ggg                              33

SEQ ID NO: 44           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 44
ggaggaggag gctagctaca acgagaggcc ggg                              33

SEQ ID NO: 45           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 45
gcccccgag gctagctaca acgaaaggag gag                               33

SEQ ID NO: 46           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 46
ccggggagag gctagctaca acgagtcctt cgg                              33

SEQ ID NO: 47           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 47
ggacagcgag gctagctaca acgagggtcc ggg                              33

SEQ ID NO: 48           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 48
tggggtggag gctagctaca acgaagcgat ggg                              33

SEQ ID NO: 49           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 49
cttgaggcag gctagctaca acgatctttc tcg                              33

SEQ ID NO: 50           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 50
cacctggtag gctagctaca acgattgagg cac                              33

SEQ ID NO: 51           moltype = DNA  length = 33
FEATURE                 Location/Qualifiers
misc_feature            1..33
```

```
                        note = Dnazyme
source                  1..33
                        mol_type = other DNA
                        organism = synthetic construct
SEQUENCE: 51
gcagggcag gctagctaca acgactggta ctt                                    33

SEQ ID NO: 52           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 52
ccagcttcag gctagctaca acgagctgtc ggg                                   33

SEQ ID NO: 53           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 53
gtgggacgag gctagctaca acgatccagc ttc                                   33

SEQ ID NO: 54           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 54
ggagtgggag gctagctaca acgagactcc agc                                   33

SEQ ID NO: 55           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 55
atgctgccag gctagctaca acgagggagt ggg                                   33

SEQ ID NO: 56           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 56
gggcggtcag gctagctaca acgagctgcc acg                                   33

SEQ ID NO: 57           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 57
gaggctccag gctagctaca acgaccaggg cgg                                   33

SEQ ID NO: 58           moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 58
gtgggtcgag gctagctaca acgagaggag gct                                   33

SEQ ID NO: 59           moltype = DNA   length = 33
FEATURE                 Location/Qualifiers
```

```
misc_feature            1..33
                        note = Dnazyme
source                  1..33
                        mol_type = other DNA
                        organism = synthetic construct
SEQUENCE: 59
aggtggtgag gctagctaca acgaggggtg gtg                                    33

SEQ ID NO: 60           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 60
tggcttctag gctagctaca acgagccctc gtc                                    33

SEQ ID NO: 61           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 61
gggctctgag gctagctaca acgagcctgg ctt                                    33

SEQ ID NO: 62           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 62
gggaccccag gctagctaca acgacggagc ccg                                    33

SEQ ID NO: 63           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 63
ggtgggggag gctagctaca acgacccacc gga                                    33

SEQ ID NO: 64           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 64
ggcgggggag gctagctaca acgaccgagg gcc                                    33

SEQ ID NO: 65           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 65
gggctgggag gctagctaca acgagggcag gga                                    33

SEQ ID NO: 66           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 66
cgtcgaggag gctagctaca acgaccgccc ctc                                    33

SEQ ID NO: 67           moltype = DNA  length = 33
```

```
                                     -continued

FEATURE                 Location/Qualifiers
misc_feature            1..33
                        note = Dnazyme
source                  1..33
                        mol_type = other DNA
                        organism = synthetic construct
SEQUENCE: 67
gggctggcag gctagctaca acgacttccc gta                                    33

SEQ ID NO: 68           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 68
cgatgcccag gctagctaca acgaccgggg cgg                                    33

SEQ ID NO: 69           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 69
gctccacgag gctagctaca acgagcccat ccg                                    33

SEQ ID NO: 70           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 70
ccggctccag gctagctaca acgagatgcc cat                                    33

SEQ ID NO: 71           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 71
tctccgcaag gctagctaca acgaccggct cca                                    33

SEQ ID NO: 72           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 72
ccgtcagcag gctagctaca acgagtctcc gca                                    33

SEQ ID NO: 73           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 73
tccccggcag gctagctaca acgacggctc ggt                                    33

SEQ ID NO: 74           moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 74
actcgggcag gctagctaca acgagtaggg cgg                                    33
```

```
SEQ ID NO: 75              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 75
ggagctgtag gctagctaca acgatcgggc acg                                    33

SEQ ID NO: 76              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 76
ggacttgcag gctagctaca acgaccgaag ccg                                    33

SEQ ID NO: 77              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 77
gggcctggag gctagctaca acgattgcat ccg                                    33

SEQ ID NO: 78              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 78
tgtgctggag gctagctaca acgacgggcc ttg                                    33

SEQ ID NO: 79              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 79
gttcacacag gctagctaca acgatccctg cct                                    33

SEQ ID NO: 80              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 80
cagttcacag gctagctaca acgaactccc tgc                                    33

SEQ ID NO: 81              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 81
cacagttcag gctagctaca acgaacactc cct                                    33

SEQ ID NO: 82              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 82
gttgccccag gctagctaca acgaagttca cac                                    33
```

-continued

```
SEQ ID NO: 83              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 83
tcgccgccag gctagctaca acgaagtggg gtc                                    33

SEQ ID NO: 84              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 84
cccgtgccag gctagctaca acgactcgcc gcc                                    33

SEQ ID NO: 85              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 85
ggcgttgcag gctagctaca acgaaggtag tgt                                    33

SEQ ID NO: 86              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 86
tggcttctag gctagctaca acgagccctc gtc                                    33

SEQ ID NO: 87              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 87
cccccgcgag gctagctaca acgagctcgt ccg                                    33

SEQ ID NO: 88              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 88
gtagggagag gctagctaca acgacccagg ctg                                    33

SEQ ID NO: 89              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 89
gggcgggcag gctagctaca acgacaaggc gcc                                    33

SEQ ID NO: 90              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 90
```

```
cgggaaggag gctagctaca acgatcgccc gcg                                   33

SEQ ID NO: 91             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 91
tagtcctcag gctagctaca acgagcggcc ccg                                   33

SEQ ID NO: 92             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 92
tccccgacag gctagctaca acgactccag tcc                                   33

SEQ ID NO: 93             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 93
tttccccgag gctagctaca acgaacctcc agt                                   33

SEQ ID NO: 94             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 94
tgagcgcgag gctagctaca acgacctcag ttt                                   33

SEQ ID NO: 95             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 95
ggaccacaag gctagctaca acgaaggtgg ttg                                   33

SEQ ID NO: 96             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 96
cttggaccag gctagctaca acgaaacagg tgg                                   33

SEQ ID NO: 97             moltype = DNA   length = 33
FEATURE                   Location/Qualifiers
misc_feature              1..33
                          note = Dnazyme
source                    1..33
                          mol_type = other DNA
                          organism = synthetic construct
SEQUENCE: 97
aaacttggag gctagctaca acgacacaac agg                                   33

SEQ ID NO: 98             moltype = DNA   length = 33
FEATURE                   Location/Qualifiers
misc_feature              1..33
                          note = Dnazyme
source                    1..33
                          mol_type = other DNA
                          organism = synthetic construct
```

```
SEQUENCE: 98
ctgattaaag gctagctaca acgattggac cac                                           33

SEQ ID NO: 99              moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 99
tggtgctgag gctagctaca acgataaact tgg                                           33

SEQ ID NO: 100             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 100
tgatgatcag gctagctaca acgactctgt ctg                                           33

SEQ ID NO: 101             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 101
tggtgatgag gctagctaca acgacatctc tgt                                           33

SEQ ID NO: 102             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 102
gcttggtgag gctagctaca acgagatcat ctc                                           33

SEQ ID NO: 103             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 103
atgggaacag gctagctaca acgaccgccg tcc                                           33

SEQ ID NO: 104             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 104
gaatgggaag gctagctaca acgaatccgc cgt                                           33

SEQ ID NO: 105             moltype = DNA   length = 33
FEATURE                    Location/Qualifiers
misc_feature               1..33
                           note = Dnazyme
source                     1..33
                           mol_type = other DNA
                           organism = synthetic construct
SEQUENCE: 105
tgacaggaag gctagctaca acgagggaac atc                                           33

SEQ ID NO: 106             moltype = DNA   length = 33
FEATURE                    Location/Qualifiers
misc_feature               1..33
                           note = Dnazyme
source                     1..33
                           mol_type = other DNA
```

-continued

```
                        organism = synthetic construct
SEQUENCE: 106
agtaaatgag gctagctaca acgaaggaat ggg                                 33

SEQ ID NO: 107          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 107
cacagtaaag gctagctaca acgagacagg aat                                 33

SEQ ID NO: 108          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 108
gcccggccag gctagctaca acgaagtaaa tga                                 33

SEQ ID NO: 109          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 109
ccacaaacag gctagctaca acgacctgta gtg                                 33

SEQ ID NO: 110          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 110
gtccacaaag gctagctaca acgaatcctg tag                                 33

SEQ ID NO: 111          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 111
ccacgtccag gctagctaca acgaaaacat cct                                 33

SEQ ID NO: 112          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 112
ccaagaccag gctagctaca acgagtccac aaa                                 33

SEQ ID NO: 113          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 113
ccaccaagag gctagctaca acgacacgtc cac                                 33

SEQ ID NO: 114          moltype = DNA   length = 33
FEATURE                 Location/Qualifiers
misc_feature            1..33
                        note = Dnazyme
source                  1..33
```

-continued

```
                                mol_type = other DNA
                                organism = synthetic construct
SEQUENCE: 114
gctggtccag gctagctaca acgacaagac cac                                33

SEQ ID NO: 115          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 115
gctctggtag gctagctaca acgacgccag tgg                                33

SEQ ID NO: 116          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 116
ctgcacccag gctagctaca acgattgccg ctc                                33

SEQ ID NO: 117          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 117
cacactgcag gctagctaca acgaccactt gcc                                33

SEQ ID NO: 118          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 118
ctttccacag gctagctaca acgatgcacc cac                                33

SEQ ID NO: 119          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 119
gcctttccag gctagctaca acgaactgca ccc                                33

SEQ ID NO: 120          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 120
ttcctggcag gctagctaca acgagctgcc ctc                                33

SEQ ID NO: 121          moltype = DNA  length = 33
FEATURE                 Location/Qualifiers
misc_feature            1..33
                                note = Dnazyme
source                  1..33
                                mol_type = other DNA
                                organism = synthetic construct
SEQUENCE: 121
gtggacgtag gctagctaca acgaaggcgg ttt                                33

SEQ ID NO: 122          moltype = DNA  length = 33
FEATURE                 Location/Qualifiers
misc_feature            1..33
                                note = Dnazyme
```

```
source                  1..33
                        mol_type = other DNA
                        organism = synthetic construct
SEQUENCE: 122
ccgggtggag gctagctaca acgagtacag gcg                              33

SEQ ID NO: 123          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 123
cctggcgcag gctagctaca acgaccagtg cgc                              33

SEQ ID NO: 124          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 124
caaatgaaag gctagctaca acgattcctg gcg                              33

SEQ ID NO: 125          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 125
tttcccaaag gctagctaca acgagaaact tcc                              33

SEQ ID NO: 126          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 126
attgttggag gctagctaca acgagccccc ttg                              33

SEQ ID NO: 127          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 127
tgggtcacag gctagctaca acgatgttgg acg                              33

SEQ ID NO: 128          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 128
tctgggtcag gctagctaca acgaattgtt gga                              33

SEQ ID NO: 129          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 129
gcacaatcag gctagctaca acgactgggt cac                              33

SEQ ID NO: 130          moltype = DNA  length = 33
FEATURE                 Location/Qualifiers
misc_feature            1..33
```

```
                        note = Dnazyme
source                  1..33
                        mol_type = other DNA
                        organism = synthetic construct
SEQUENCE: 130
ggagcacaag gctagctaca acgacatctg ggt                                       33

SEQ ID NO: 131          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 131
actggagcag gctagctaca acgaaatcat ctg                                       33

SEQ ID NO: 132          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 132
atggagggag gctagctaca acgatggagc aca                                       33

SEQ ID NO: 133          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 133
tggtacttag gctagctaca acgaggaggg act                                       33

SEQ ID NO: 134          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 134
gggctggtag gctagctaca acgattatgg agg                                       33

SEQ ID NO: 135          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 135
tcaacgatag gctagctaca acgagcagcc ggg                                       33

SEQ ID NO: 136          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 136
cctcaacgag gctagctaca acgaatgcag ccg                                       33

SEQ ID NO: 137          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 137
tcacctcaag gctagctaca acgagatatg cag                                       33

SEQ ID NO: 138          moltype = DNA  length = 33
FEATURE                 Location/Qualifiers
```

```
misc_feature            1..33
                        note = Dnazyme
source                  1..33
                        mol_type = other DNA
                        organism = synthetic construct
SEQUENCE: 138
cgtcgttcag gctagctaca acgactcaac gat                                    33

SEQ ID NO: 139          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 139
gtaaagatag gctagctaca acgagcgtgt tgg                                    33

SEQ ID NO: 140          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 140
aagtaaagag gctagctaca acgaatgcgt gtt                                    33

SEQ ID NO: 141          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 141
ggcaatgaag gctagctaca acgatgggtt tct                                    33

SEQ ID NO: 142          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 142
tcacggcaag gctagctaca acgagaactg ggt                                    33

SEQ ID NO: 143          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 143
aggcagtcag gctagctaca acgaggcaat gaa                                    33

SEQ ID NO: 144          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 144
atctcggcag gctagctaca acgatctggt agg                                    33

SEQ ID NO: 145          moltype = DNA  length = 33
FEATURE                 Location/Qualifiers
misc_feature            1..33
                        note = Dnazyme
source                  1..33
                        mol_type = other DNA
                        organism = synthetic construct
SEQUENCE: 145
gctgagtaag gctagctaca acgactcggc att                                    33

SEQ ID NO: 146          moltype = DNA  length = 33
```

```
FEATURE                 Location/Qualifiers
misc_feature            1..33
                        note = Dnazyme
source                  1..33
                        mol_type = other DNA
                        organism = synthetic construct
SEQUENCE: 146
tattatcaag gctagctaca acgatttcag ctg                                     33

SEQ ID NO: 147          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 147
gggttattag gctagctaca acgacaattt tca                                     33

SEQ ID NO: 148          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 148
aaggggttag gctagctaca acgatatcaa ttt                                     33

SEQ ID NO: 149          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 149
ctcccggaag gctagctaca acgacctttg gca                                     33

SEQ ID NO: 150          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 150
gtacatggag gctagctaca acgatcaaag ttc                                     33

SEQ ID NO: 151          moltype = DNA   length = 33
FEATURE                 Location/Qualifiers
misc_feature            1..33
                        note = Dnazyme
source                  1..33
                        mol_type = other DNA
                        organism = synthetic construct
SEQUENCE: 151
aactgggtag gctagctaca acgaggcaga ata                                     33

SEQ ID NO: 152          moltype = DNA   length = 33
FEATURE                 Location/Qualifiers
misc_feature            1..33
                        note = Scrambled dnazyme control
source                  1..33
                        mol_type = other DNA
                        organism = synthetic construct
SEQUENCE: 152
tgtgatgtag gctagctaca acgacagatg gaa                                     33

SEQ ID NO: 153          moltype = DNA   length = 19
FEATURE                 Location/Qualifiers
misc_feature            1..19
                        note = GATA3 forward primer
source                  1..19
                        mol_type = other DNA
                        organism = synthetic construct
SEQUENCE: 153
gaaccggccc cttatcaag                                                     19
```

```
SEQ ID NO: 154          moltype = DNA   length = 19
FEATURE                 Location/Qualifiers
misc_feature            1..19
                        note = GATA3 reverse primer
source                  1..19
                        mol_type = other DNA
                        organism = synthetic construct
SEQUENCE: 154
acagttcgcg caggatgtc                                                    19

SEQ ID NO: 155          moltype = DNA   length = 21
FEATURE                 Location/Qualifiers
misc_feature            1..21
                        note = GAPDH forward primer
source                  1..21
                        mol_type = other DNA
                        organism = synthetic construct
SEQUENCE: 155
aggtcggtgt gaacggattt g                                                 21

SEQ ID NO: 156          moltype = DNA   length = 23
FEATURE                 Location/Qualifiers
misc_feature            1..23
                        note = GAPDH reverse primer
source                  1..23
                        mol_type = other DNA
                        organism = synthetic construct
SEQUENCE: 156
tgtagaccat gtagttgagg tca                                               23

SEQ ID NO: 157          moltype = DNA   length = 23
FEATURE                 Location/Qualifiers
misc_feature            1..23
                        note = IL-6 forward primer
source                  1..23
                        mol_type = other DNA
                        organism = synthetic construct
SEQUENCE: 157
tagtccttcc tacccccaatt tcc                                              23

SEQ ID NO: 158          moltype = DNA   length = 21
FEATURE                 Location/Qualifiers
misc_feature            1..21
                        note = IL-6 reverse primer
source                  1..21
                        mol_type = other DNA
                        organism = synthetic construct
SEQUENCE: 158
ttggtcctta gccactcctt c                                                 21

SEQ ID NO: 159          moltype = DNA   length = 21
FEATURE                 Location/Qualifiers
misc_feature            1..21
                        note = IL-10 forward primer
source                  1..21
                        mol_type = other DNA
                        organism = synthetic construct
SEQUENCE: 159
gctcttactg actggcatga g                                                 21

SEQ ID NO: 160          moltype = DNA   length = 20
FEATURE                 Location/Qualifiers
misc_feature            1..20
                        note = IL-10 reverse primer
source                  1..20
                        mol_type = other DNA
                        organism = synthetic construct
SEQUENCE: 160
cgcagctcta ggagcatgtg                                                   20
```